United States Patent
Saito et al.

(10) Patent No.: US 6,215,843 B1
(45) Date of Patent: *Apr. 10, 2001

(54) X-RAY CT SCANNER USING X-RAY DETECTOR ACQUIRING MULTI-SLICE DATA OF UNEQUAL SLICE PITCHES

(75) Inventors: Yasuo Saito; Katsuyuki Taguchi, both of Nishinasuno-machi; Hiroshi Aradate, Otawara, all of (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/960,594

(22) Filed: Oct. 30, 1997

(30) Foreign Application Priority Data

Oct. 30, 1996 (JP) .................................................. 8-288528

(51) Int. Cl.[7] .................................................... G01N 23/00
(52) U.S. Cl. ......................................... 378/19; 250/370.09
(58) Field of Search ........................ 378/19; 250/370.09, 250/370.11

(56) References Cited

U.S. PATENT DOCUMENTS 4,965,726 * 10/1990 Heuscher ................................ 378/19

* cited by examiner

Primary Examiner—Craig E. Church
(74) Attorney, Agent, or Firm—Oblon, Spivak, McClelland, Maier & Neustadt, P.C.

(57) ABSTRACT

An X-ray CT scanner for producing a CT image of a subject by scanning an X-ray fan beam radiated an X-ray source through the subject in a predetermined slice-thickness direction. The scanner comprises a main detector detecting the X-ray beam to produce an X-ray transmission data of a subject and to a plurality of slices in agreement with unequal segment pitches. The detector comprises a two-dimensional array consisting of a plurality of X-ray detecting elements receiving the X-ray beam and being disposed in the slice-thickness direction as a row line and a channel direction as a column line. The X-ray detection sensitivity distributions of all the segments formed by the detecting elements disposed in predetermined element pitches in the slice-thickness direction are adjusted to be uniform or approximately uniform by controlling various members, devices, or factors which are all controllable for X-ray detection sensitivity, thereby enabling the X-ray transmission data of unequal slice thicknesses to be adjusted in sensitivity slice by slice in the detector. The scanner further comprises a switch group selecting and combining the sensitivity-adjusted X-ray transmission data of the plurality of slices, the selected and combined X-ray transmission data being provided to selected ones of a data acquiring elements of a data acquisition system.

37 Claims, 17 Drawing Sheets

X-RAY CT SCANNER USING X-RAY DETECTOR ACQUIRING MULTI-SLICE DATA OF UNEQUAL SLICE PITCHES

BACKGROUND OF THE INVENTION

1. Field of the Invention

The present invention relates to an X-ray CT scanner including a two-dimensional detector that has a plurality of detecting elements laid out two-dimensionally in the slice-thickness and channel directions thereof in a manner such that a plurality of segments having different slice thicknesses are formed in the slice-thickness direction for multi-slice scanning, the sensitivity distributions of the segments being uniformed in the slice-thickness direction. In the invention, the slice-thickness direction (or simply, slice direction or segment direction) corresponds to the direction of the rotation axis of a gantry of the scanner.

2. Description of the Related Art

X-ray CT scanners include a fan-beam (single-slice)X-ray CT scanner that has been adopted in the past.

The fan-beam X-ray CT scanner has an X-ray source and detector opposed to each other with a subject (for example, a patient) between them. The detector has detecting elements, which constitute, for example, approximately 1000 channels, arranged in the form of a sector in a (channel)direction orthogonal to a body-axial direction of the subject.

Though a variety of types of detector can be used as the X-ray detector, a scintillation detector, which is easily compacted, is frequently employed. The scintillation detector has a scintillator functioning as an X-ray detecting element (segment) and a photo sensor such as photodiode. X-rays transmitted through a subject are received by the scintillator, in which fluorescence is generated in response to the reception. The fluorescence is converted into an electric signal by the photo sensor. The electric signal constitutes X-ray transmittance data to be outputted from the detector segment by segment.

In the X-ray CT scanner, a fan-shaped X-ray beam is irradiated from the X-ray source to a certain slice plane (or, simply, a slice) set in the subject. An X-ray beam transmitted by the slice plane of the subject is detected by the detector, and then X-ray transmission data is acquired.

The acquired X-ray transmission data is sent to a data acquisition system (DAS) having data acquiring elements associated with the detecting elements of the detector. Each element carries out amplification or the like and acquires projection data (one data acquisition is referred to as one view).

While the X-ray source and detector are rotated in unison about the subject, X-rays are irradiated and data acquisition is repeated approximately 1000 times. Consequently, projection data in multiple directions of the subject is acquired. Based on the projection data in multiple directions, the image of the slice plane of the subject is reconstructed.

In such a single-slice X-ray CT scanner, the image of a certain slice plane of a subject is produced. It is therefore hard to produce images of a wide range of the subject for a short period of time. There is therefore an increasing demand from doctors and the like for producing high-definition (high-resolution) images of a wide range of a subject for a unit period of time.

In an effort to meet the demand, studies have been made on a multi-slice X-ray CT scanner in recent years.

The multi-slice X-ray CT scanner has a plurality of columns (a plurality of (N) segments) of detecting elements, each of which is the same as the one employed in the single-slice X-ray CT scanner, in the body-axis direction of a subject (also referred to as a slice-thickness direction or segment direction). The detecting elements constitute a two-dimensional detector having detecting elements numbering the product of M channels by N segments. In this case, elements of a DAS are associated with the detecting elements of the two-dimensional detector.

In other words, the multi-slice X-ray CT scanner has an X-ray source for bombarding a conical X-ray beam, and the foregoing two-dimensional detector. X-rays of the conical X-ray beam (diameter of an effective field of view, FOV) passing through a subject are detected by the two-dimensional detector, whereby projection data of multiple slice planes of the subject is acquired at a time. Thus, the multi-slice X-ray CT scanner is expected to enable acquisition of high-definition images from a wide range.

Various proposals have been made of the configurations of such a multi-slice X-ray CT scanner and two-dimensional detector employed in the multi-slice X-ray CT scanner.

For example, known is an idea of freely changing one slice thickness by combining X-ray data items detected by a plurality of segments through image post-processing based on detected data.

Thinking of the specifications of a two-dimensional detector and DAS for a multi-slice X-ray CT scanner, several parameters have significant meanings. To be more specific, for improving the resolution in a body-axis direction, it is necessary to finely set the pitches in the body-axis direction of elements corresponding to segments of the detector (slice thickness) relative to adjoining ones. For expanding a scanned region in the body-axis direction (for eventually shortening the scan tome of a certain region, the size of the whole detector (the number of columns corresponding to the segments of the detector) must be made larger. In an effort to clear both the requirements that are seemingly contradictory, that is, improvement of the resolution in the body-axis direction and expansion of a scanned region, it has been conceived that sufficiently small detecting elements that are fine divisions of a detector are arranged in the body-axis direction by the number of columns (segments) defining a sufficiently large size.

However, on the detector side, there are limitations in a minimum size of an element (in a slice-thickness direction) and a maximum number of elements because of the problems that geometrical efficiency is deteriorated with finer segmentation of the detector and that the density of wiring patterns increase with an increase in number of elements. It is therefore currently thought that approximately 1 mm and approximately 30 columns are feasible levels of the minimum size of an element and of the maximum number of columns of elements respectively.

For arranging approximately 30 columns of detecting elements, it is necessary to install a DAS having the number of elements corresponding to the number of segments or columns of the detecting elements. A simple countermeasure is to arrange a plurality of (30) columns of currently-employed DASs. In reality, there are limitations in the number of elements of a DAS that can be arranged because of the problem of preserving an installation space in a scanner system or the problem of ensuring appropriate cost performance. The existing high-density installation technology and manufacturing cost permit about 10 columns of elements as a level feasible in the near future.

Since restrictions are thus placed differently on the parameters such as the number of elements of a DAS, a minimum size of an element of a detector, and a maximum number of elements in the detector, it is hard to attain high resolution in the body-axis Direction and a wide scanned region by nonchalantly combining these parameters. A further commitment to novelties and improvements is requested.

On one hand, in the case that the scintillation type detector (i.e., solid detector) incorporating a combination of scintillators and photo sensors is used, light is absorbed at the edges in the slice-thickness direction of the scintillator. Due to this light absorption, know is that the sensitivity distribution of each scintillator is dropped at the edge portions in the slice-thickness direction of its X-ray incidence area. Understood from this fact is that sensitivities (amounts of output light per unit size) at the edge portions of a scintillator depend on its sizes (i.e., width in the slice-thickness). In other words, the thinner the slice thickness, the lower the entire sensitivity of a detector, because the lowered sensitivities at the edge portions of a scintillator having thinner slices have larger influence on the entire sensitivity.

Owing to this, when an X-ray detector is provided a plurality of detecting segments mutually different in slice thickness, irregularities in sensitivity distributions of segments are brought about depending on differences in slice thicknesses, which will cause artifacts in reconstructed X-ray images.

SUMMARY OF THE INVENTION

The present invention attempts to break through the foregoing circumstances. The first of the present invention is to provide a multi-slice X-ray CT scanner capable of not only realizing both high resolution in a slice-thickness direction for an object and a wide scanned region in the slice-thickness direction but also providing X-ray reconstructed images of less artifacts (higher image quality) by eliminating irregularities in sensitivity distribution for detecting X-rays resultant from production of detection signals of unequal slice thicknesses.

The second object of the present invention is to provide a multi-slice X-ray XT scanner offering the greatly increased freedom in selecting a slice thickness.

For accomplishing the above objects, according to the first aspect of the present invention, there is provided an X-ray CT scanner for producing a computed tomography (CT) image of a subject by scanning an X-ray fan beam radiated an X-ray source through the subject in a predetermined slice-thickness direction, the scanner comprising: means for detecting the X-ray beam transmitted through the subject to produce an X-ray transmission data in electric quantity corresponding to the transmitted X-ray beam and to a plurality of slices in agreement with unequal segment pitches, the X-ray transmission data being adjusted in sensitivity slice by slice, the detecting means comprising a two-dimensional array consisting of a plurality of X-ray detecting elements receiving the X-ray beam and being disposed in the slice-thickness direction as a row line and a channel direction orthogonal to the slice-thickness direction as a column line; and means for acquiring the X-ray transmission data to be reconstructed into the CT image.

It is preferred that the acquiring means comprises a data acquisition system in which a plurality of data acquiring elements are two-dimensionally disposed in the slice-thickness and channel directions, the scanner further comprising means for selecting and combining the sensitivity-adjusted X-ray transmission data of the plurality of slices, the selected and combined X-ray transmission data being provided to selected ones of the data acquiring elements. It is still preferred that each of the X-ray detecting elements comprises a first converting element converting the transmitted X-ray beam to a light signal and a second converting element converting the light signal to an electric signal constituting the X-ray transmission data, the first converting elements in the array being disposed in equal element pitches in the slice-thickness direction and the second converting elements in the array being disposed in the element unequal pitches in the slice-thickness direction. Preferably, the first converting element is a scintillator and the second converting element is a photo sensor.

As another aspect of the invention, it is preferred that each of the X-ray detecting elements comprises a first converting element converting the transmitted X-ray beam to a light signal and a second converting element converting the light signal to an electric signal constituting the X-ray transmission data, both the first and second converting elements in the array being disposed in unequal element pitches in the slice-thickness direction, and wherein the X-ray beam detecting means comprises a filter member inserted in the first and second converting elements of each X-ray detecting element, the filter member has a light-transmittance changed depending on the unequal segment pitches. For example, the filter member is constructed such that the light-transmittance is externally controllable. In this case, for example, it is also preferred that the X-ray beam detecting means comprises means for changing the light-transmittance according to at least one of a desired sensitivity distribution for the X-ray transmission data provided to the acquiring means, a scanning condition for obtaining the CT image, and a selecting condition the X-ray transmission data of the plurality of slices in the selecting and combining means.

Still, another aspect of the invention is that the X-ray detecting elements in each row line is disposed in unequal element pitches reflecting a plurality of kinds of element pitches in the slice-thickness direction, a plurality of selected ones of the X-ray detecting elements in each row line being the same in element pitch, and wherein the X-ray beam detecting means comprises means for adjusting sensitivity of the X-ray detecting elements row line by row line.

For example, the plurality of kinds of element pitches are two in kind, thus forming a first element pitch and a second element pitch being applied to the selected X-ray detecting elements, and wherein each of the X-ray detecting elements comprises a first converting element converting the transmitted X-ray beam to a light signal and a second converting element converting the light signal to an electric signal constituting the x-ray transmission data. The first converting element is a scintillator and the second converting element is a photo sensor, for example. Preferably, the sensitivity adjusting means comprises a combining lead member for not only electrically combining outputs of the photodiodes corresponding to the selected X-ray detecting elements according to the unequal segment pitches but also providing the combined outputs to the data acquiring means and a light-reflecting member partially covered on each of light incidence areas of the photodiodes corresponding to the selected X-ray detecting elements according to the unequal segment pitches.

According to the invention, X-ray beams which have transmitted a subject are received by an array in which a plurality of X-ray detecting elements are two-dimensionally disposed. The elements forms a plurality of groups of segments in the slice-thickness direction, each group having a different slice thickness from other group. When the transmitted X-ray beams are detected by the detecting elements, the detected signals as X-ray transmittance data are according to a plurality of slices and unequal segment pitches (i.e., unequal slice thicknesses) in the slice-thickness direction, independently of disposed pitches of the X-ray detecting elements. Additionally, since the sensitivity distributions all the segment groups (or all the detecting elements) are adjusted to be uniform by various configurations which includes improved element constructions, arrangement of members whose optical characteristics are changed, improved combination of detection outputs, or the like. The detected X-ray transmission data of each slice are the same or approximately the same in sensitivity.

The sensitivity-adjusted detection signals constituting X-ray transmittance data of a plurality of slices of designated unequal slice thicknesses are electrically combined in the slice-thickness direction by the selecting and combining means according to slice conditions including requirements for slice thickness. The combined signals are then provided to the acquiring means which can be realized by a DAS.

In other words, any combination of a plurality of slices of sensitivity-adjusted data can be done. Therefore, both high resolution (fine slice pitch) in the slice-thickness direction and a wide scanned region therein can be realized. Additionally, owing to the sensitivity adjustment of the segments in the slice-thickness direction, irregularities in the sensitivity distributions of the segments can suitably be eliminated in that direction, thereby artifacts in reconstructed images being suppressed at low levels and image quality being upgraded markedly. Consequently, the diagnostic performance of the X-ray CT scanner (multi-slice X-ray CT scanner) having the two-dimensional detector can be improved, the practicality thereof can be improved, and the diagnostic precision and efficiency of the X-ray CT scanner can be improved.

Further advantages of the present invention will become apparent upon reading and understanding the following detailed description of the preferred embodiments.

DESCRIPTION OF THE PREFERRED EMBODIMENTS

Referring to the appended drawings, an embodiment of the present invention will be described below.

Figure 1:
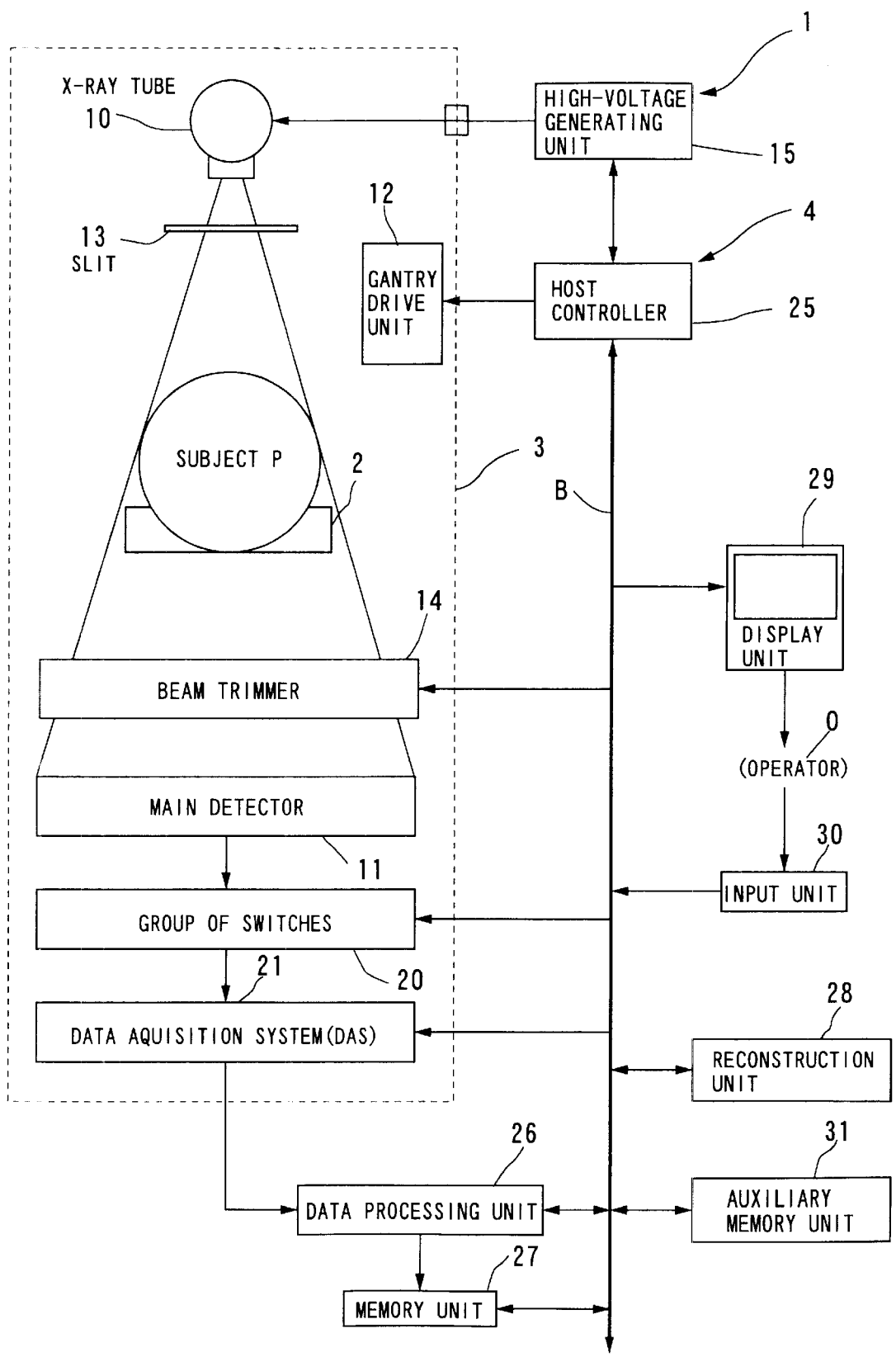
FIG. 1 is a block diagram schematically showing the configuration of an X-ray CT scanner in accordance with embodiments of the present invention.

FIG. 1 is a block diagram showing the schematic configuration of an X-ray CT scanner of 1 of an embodiment.

Referring to FIG. 1, the X-ray CT scanner (CT system) 1 comprises a patient couch 2 on which a subject (patient) P lies down, a gantry 3 having a diagnostic bore, which is not shown, into which the subject P is inserted for diagnosis and acquiring projection data of the subject P, and a system unit 4 for controlling the whole scanner, reconstructing an image on the basis of the acquired projection data, and displaying a reconstructed image.

The patient couch 2 can slide in body-axis directions of the subject P when driven by a couch drive unit that is not shown.

The gantry 3 has an X-ray tube 10 and main detector 11 opposed with the subject P inserted in the diagnostic bore between them, and further includes a gantry drive unit 12. The X-ray tube 10 and main detector 11 can be rotated in unison about a center axis parallel to a body-axis direction of the subject P inserted into the diagnostic bore of the gantry 3 when driven by the gantry drive unit 12. Interposed between the X-ray tube 10 and subject P in the gantry 3 is a slit 13 for reshaping a conical X-ray beam bombarded from the X-ray focal spot in the X-ray tube 10, and thus produce an X-ray beam of a desired size. Located on the incident side of an X-ray beam of the main detector 11 is a beam trimmer 14 having two X-ray shielding plates that move in, for example, column directions of the main detector 11. The beam trimmer 14 trims an X-ray beam passing through the subject P by controlling the positions in the row directions of the main detector 11 to which the two shielding plates are moved according to a condition for scanning (including the condition of a slice thickness), and thus produces a transmitted X-ray beam exhibiting a good transmission profile.

Furthermore, the X-ray CT scanner 1 includes a high-voltage generating unit 15 for applying a high voltage to the X-ray tube 10. Application of a high voltage to the X-ray tube 10 by means of the high-voltage generating unit 15 is achieved by, for example, a contact type slip ring mechanism.

The main detector 11 is constructed as a scintillation type of detector incorporating therein scintillators and photo sensors, such as photodiodes. The scintillators receives X-rays irradiated by the X-ray tube 10 and transmitted through a subject, and the photo sensors output electric detection signals converted from fluorescence.

Figure 2:
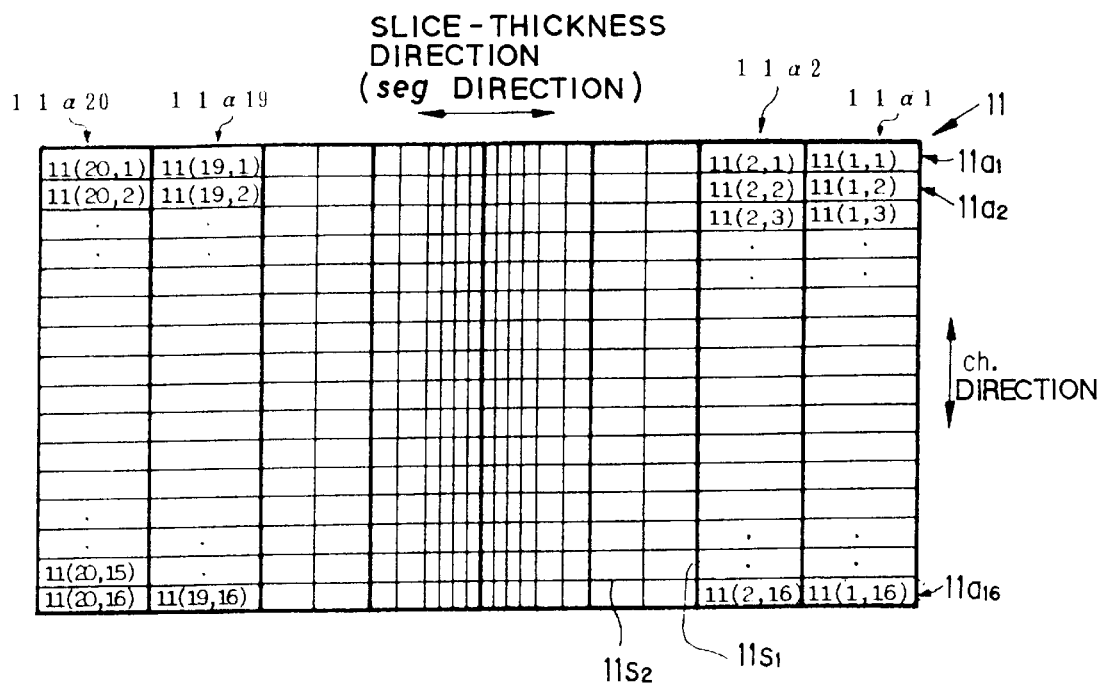
FIG. 2 shows the structure of a two-dimensional main detector according to a first embodiment of the present invention.

The main detector 11 of scintillation type is, as shown in FIG. 2, realized as a two-dimensional X-ray detector in which a plurality of rows of detecting elements, each of which has a plurality of segments (20 segments in this embodiment) arranged in a segment direction (body-axis direction or slice-thickness direction) and constitute one channel, are laid out in the form of an array in a channel direction in order to constitute a plurality of channels (16 channels in this embodiment)(FIG. 2 shows a two-dimensional detector having an array of 16 channels by 20 segments).

In other words, in FIG. 2, assuming that a row of elements constituting the first channel, which covers 20 segments, is a row of elements 11a1, rows of elements 11a1 to 11a16 constituting the first to sixteenth channels are arranged. Assuming that a column of elements constituting 16 channels which covers the first segment is a column of elements 11α1, columns of elements 11α1 to 11α20 covering the first to twentieth segments are arranged.

Herein, assuming that the position (address) of each of the detecting elements laid out two-dimensionally is expressed in the format of (segment, channel), an element belonging to the first segment and first channel is expressed as an element 11(1,1). The elements belonging to the row of elements 11a1 constituting the first channel are expressed as elements 11(2,1), etc., and 11(20,1). Likewise, the elements belonging to the remaining rows of elements 11a2 to 11a16 are expressed as follows: the elements belonging to the row of elements 11a2 constituting the second channel are expressed as elements 11(1,2), etc., and 11(20,2); the elements belonging to the row of elements 11a3 constituting the third channel are expressed as elements 11(1,3), etc., and 11(20, 3); the elements belonging to the row of elements 11a15 constituting the fifteenth channel are expressed as elements 11(1,15), etc., and 11(20,15); and the elements belonging to the row of elements 11a16 constituting the sixteenth channel are expressed as elements 11(1,16), etc., and 11(20, 16).

Separators (reflector plates) 11s1 and 11s2 made of, for example, a metal are interposed between segments and channels respectively, whereby crosstalk between adjoining channels and segments is eliminated.

The main detector 11 is constructed such that it receives X-rays transmitted through a subject P and finally produces detection signals for a plurality of slices in agreement with unequal slice thicknesses. According to a specified slice condition, the detection signals according to the unequal slice thicknesses are combined into X-ray transmission row data of a plurality of slices having the slice thickness or different slice thicknesses.

Since thicknesses (slice pitches) realized with the widths in a segment direction of the elements of each of the rows of elements 11a1 to 11a16 constituting the channels of the main detector (two-dimensional detector) 11 of this embodiment are made unequal so that the slice thicknesses get larger from the center element toward the elements on both ends. The slice pitches that are unequal in the segment direction shall be referred to as unequal pitches.

Figure 3:
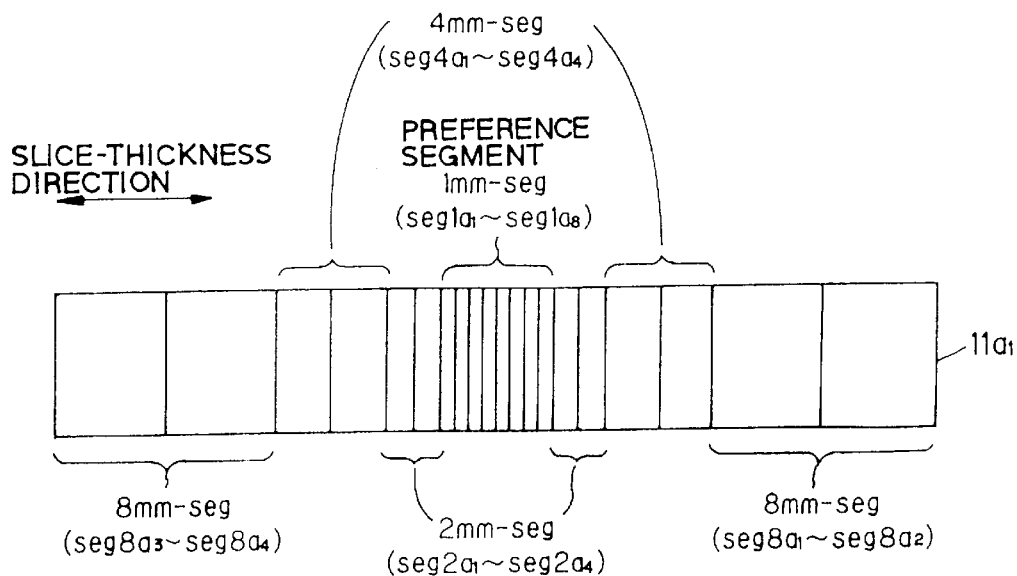
FIG. 3 shows the structure of a row of detecting elements in one example of a main detector in such a connection mode that a minimum slice thickness to be realized is 1 mm and the total number of segments is 20.

FIG. 3 is concerned with the structure of each of the rows of elements 11a1 to 11a16 constituting the channels of the main detector 11. FIG. 3 shows the structure of the row of elements 11a1 constituting the first channel.

In this embodiment, a column of detecting elements having a width realizing a minimum slice thickness permitted by the X-ray CT scanner 1 is referred to as a reference segment. In this embodiment, the minimum slice thickness shall be 1 mm.

Referring to FIG. 3, the structure of each of the rows of elements 11a1 to 11a16 constituting the channels of the main detector 11 is such that eight reference segments (segments whose widths correspond to a slice thickness of 1 mm) are laid out in the center (seg1a1 to seg1a8 from the right in the drawing), a total of four segments of 2 mm wide (segments whose widths correspond to a slice thickness of 2 mm) are laid out in twos on both outer sides of the reference segments (seg2a1 to seg2a4 from the right in the drawing), a total of four segments of 4 mm wide (segments whose widths correspond to a slice thickness of 4 mm) are laid out in twos on both outer sides of the segments of 2 mm wide (seg4a1 to seg4a4 from the right in the drawing). Moreover, a total of four segments of 8 mm wide (segments whose widths correspond to a slice thickness of 8 mm) are laid out in twos on both outer sides of the segments of 4 mm wide (seg8a1 to seg8a4 from the right in the drawing). There are thus a total of 20 segments per channel. All the 20 segments come to 64 mm in width. Noted is that these dimensions are values measured in the center of the axis of rotation of the gantry 3 (X-ray tube 10 and main detector 11) but not actual dimensions in the main detector 11.

Figure 4:
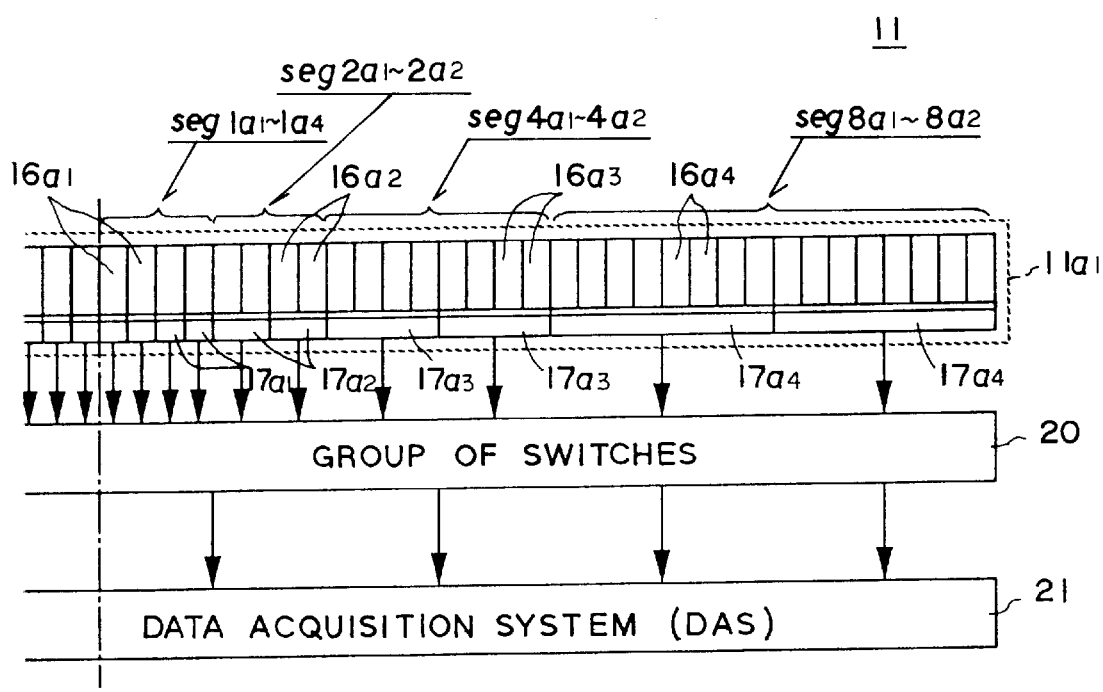
FIG. 4 is a view showing the internal structure of the column of the first channel of a main detector.

FIG. 4 shows the internal structure of a row of detecting elements 11a1 that is for the first channel and a representative of a plurality of rows of detecting elements 11a1 to 11a16 constituting the main detector 11. The foregoing unequal pitch structure is employed by this detector 11. In the FIG. 4, only half of the row 11a1, located in the right-hand side in the drawing of FIG. 3, is shown therein.

As shown in FIG. 4, the row of detecting elements 11a1 constituting the first channel has the group of reference segments seg1a1 to seg1a4 (and seg1a5 to seg1a8 not shown in FIG. 4) each having a single scintillator 16a1. In each of the reference segments seg1a1 to seg1a8, each scintillator 16a1 has an X-ray incidence surface that has the width of a slice plane equal to a slice pitch (1 mm) of each reference segment in the slice-thickness direction.

Each scintillator 16a1 is formed into a box-like shape having an X-ray incidence surface and sides in both the channel and slice-thickness directions on which a light-reflecting member is layered. Each scintillator 16a1 also has a fluorescence output surface with which a photodiodes 17a1 serving as a photo sensor is coupled to receive the fluorescence with the help of a jointing member, such as adhesive or optical compound (semi-solid state lubricant, such as grease, having an adhesion property with which the joint is performed). Each photodiodes 17a1 has an active area (not shown) that is a light-receiving area composed of pn-conjunction and the slice directional size of which equals the slice pitch (1 mm) of the reference segment. The fluorescence generated from the scintillator is then received by the active area of the photodiode to convert it into an electric signal, to be outputted.

The row 11a1 also has the 2 mm-wide segments seg2a1 and seg2a2 (and seg2a3 and seg2a4 not shown in FIG. 4) each having two scintillator 16a2 and 16a2 disposed in the slice-thickness direction. Each scintillator 16a2 comprises an X-ray incidence surface the slice-directional size of which equals the slice pitch (1 mm) of the reference segment in the slice-thickness direction.

Each scintillator 16a2 is formed into a box-like shape having an X-ray incidence surface and sides in both the channel and slice-thickness directions on which a light-reflecting member is layered. Each scintillator 16a2 also has a fluorescence output surface with which a photodiodes 17a2 serving as a photo sensor is coupled to receive the fluorescence with the help of the jointing member. Each photodiodes 17a2 has an active area (not shown) the slice directional size of which equals the slice pitch (2 mm) of the 2 mm-wide segment. The fluorescence generated from the scintillator is then received by the active area of the photodiode to convert it into an electric signal, to be outputted.

The row 11a1 also has the 4 mm-wide segments seg4a1 and seg4a2 (and seg4a3 and seg4a4 not shown in FIG. 4) each having four scintillator 16a3 . . . 16a3 disposed in the slice-thickness direction. Each scintillator 16a3 comprises an X-ray incidence surface the slice-directional size of which equals the slice pitch (1 mm) of the reference segment in the slice-thickness direction.

Each scintillator 16a3 is formed into a box-like shape having an X-ray incidence surface and sides in bot the channel and slice-thickness directions on which a light-reflecting member is layered. Each scintillator 16a3 also has fluorescence output surface with which a photodiodes 17a3 serving as a photo sensor is coupled to receive the fluorescence with the help of the jointing member. Each photodiodes 17a3 has an active area (not shown) the slice directional size of which equals the slice pitch (4 mm) of the 4 mm-wide segment. The fluorescence generated from the scintillator is then received by the active area of the photodiode to convert it into an electric signal, to be outputted.

The row 11a1 also has the 8 mm-wide segments seg8a1 and seg8a2 (and seg8a3 and seg8a4 not shown in FIG. 4) each having eight scintillator 16a4 . . . 16a4 disposed in the slice-thickness direction. Each scintillator 16a4 comprises an X-ray incidence surface the slice-directional size of which equals the slice pitch (1 mm) of the reference segment in the slice-thickness direction. Each scintillator 16a4 is formed into a box-like shape having an X-ray incidence surface and sides in both the channel and slice-thickness directions on which a light-reflecting member is layered. Each scintillator 16a4 also has a fluorescence output surface with which a photodiodes 17a4 serving as a photo sensor is coupled to receive the fluorescncece with the help of the jointing member. Each photodiodes 17a4 has an active area (not shown) the slice directional size of which equals the slice pitch (8 mm) of the 8 mm-wide segment. The fluorescence generated from the scintillator is then received by the active area of the photodiode to convert it into an electric signal to be outputted.

As understood from the above, the scintillator 16a1 . . . 16a1 to 16a4 . . . 16a4 group by group belonging to the segment groups are equal in slice thickness to each other and equal to the slice thickness (1 mm) of the reference segment, while the photodiodes 17a1 . . . 17a1 to 17a4 . . . 17a4 group by group belonging to the segment groups form unequal sizes in slice thickness and are in agreement with the slice thicknesses o the segments disposed.

In other words, although each reference segment is composed of a single photodiode and a single scintillator faced with each other, each 2 mm-wide segment is composed of a single photodiode and two scintillators faced with other, each 4 mm-wide segment a single photodiode and four scintillators faced with other, and each 8 mm-wide segment a single photodiode and eight scintillators faced with other.

Figure 5:
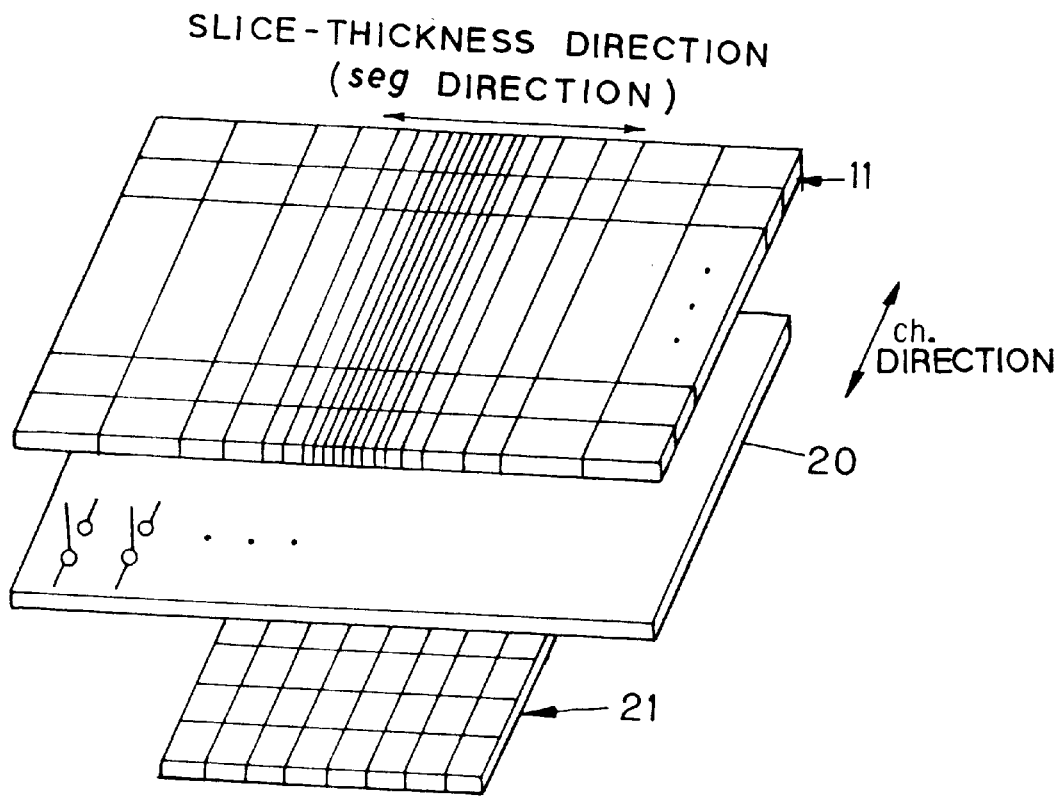
FIG. 5 is an oblique view schematically showing a main detector, a group of switches, and a data acquisition system (DAS)
Figure 6:
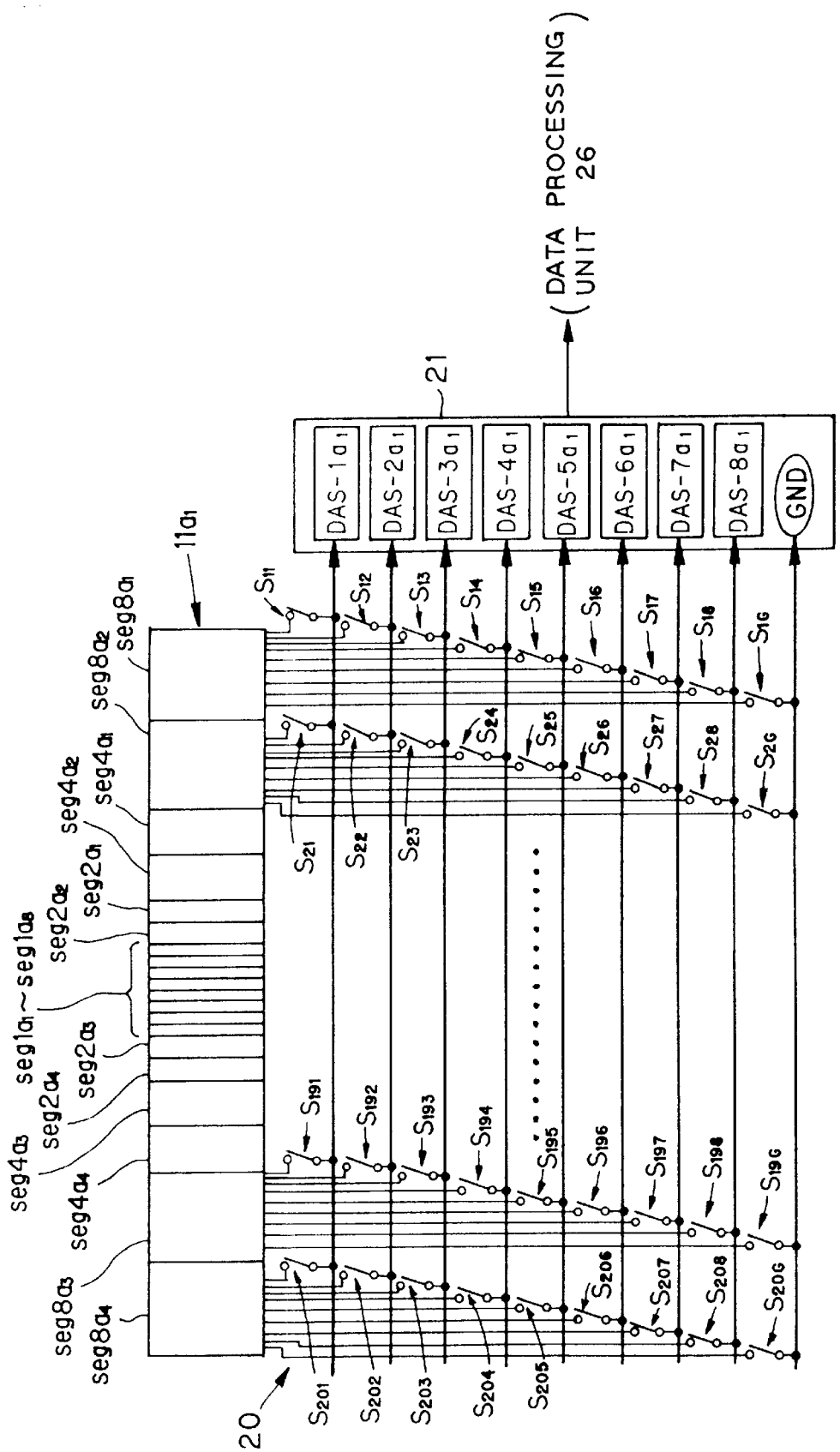
FIG. 6 is a diagram showing an example of the structure of a group of switches in such a connection mode that a DAS designed for handing 8 slices is used to acquire data.

In the main two-dimensional detector 11, the active area of each photodiode is connected to the group of switches by a lead. Each detecting element, essentially made up of the scintillator and photodiode, detects X-rays as X-ray transmittance data, and sends those data to the DAS (data acquisition system) 21 via the group of switches 20. As shown in FIG. 6, the DAS includes data acquisition elements DAS-1a1 to DAS-8a1 ( . . . DAS 1a16 to DAS-8a16) which are less in number by 8 columns (i.e., 8 slices) compared with 20 segments arranged in each of the rows of detecting elements 11a1 to 11a16. FIG. 5 is an oblique view showing the structures of the two-dimensional detector 11, group of switches 20, and DAS 21 of this embodiment. As shown in FIG. 5, the two-dimensional detector 11 has detecting elements set in array, and the group of switches 20 have switching devices such as FETs mounted on, for example, a switching substrate. Each of the detecting elements is made up of a scintillator layer, a light-transmitting resin layer, and a photodiode layer, thus X-rays reached the scintillator layer being converted to corresponding electric signals via photo signals. Alternatively, a semiconductor detecting device directly converting X-rays to electric signals may be used. The data acquisition elements of the DAS 21 are laid out in the form of an array like the detecting elements of the two-dimensional detector 11.

The data acquisition elements (DAS-1a1 to DAS-8a1, etc., and DAS-1a16 to DAS-8a16) of the DAS 21 acquire projection data of 8 slices of the subject P by amplifying supplied X-ray transmission data items and converting them into digital signals.

FIG. 6 shows the connectional relationship between the row of detecting elements 11a1 (seg1a1 to seg1a8, seg2a1 to seg2a4, seg4a1 to seg4a4, and seg8a1 to seg8a4) constituting the first channel, which covers 20 segments, within the main detector 11 and the DAS 21 having the data acquisition elements (DAS-1a1 to DAS-8a1) associated with 8 columns (8 slices) out of the row of detecting elements 11a1 constituting the first channel by way of the group of switches 20. For brevity's sake, FIG. 6 shows only a group of switches for connecting the detecting elements seg8a1 to seg8a4 on both ends of the row of detecting element to the data acquisition elements DAS-1a1 to DAS-81a.

Referring to FIG. 6, the element seg8a1 is connected to the element DAS-1a1 via a switch S11, also connected to the elements DAS-2a1 to DAS-8a1 via switches S12 to S18, and grounded via a switch S1G. Likewise, the element seg8a2 is connected to the elements DAS-1a1 to DAS-8a1 and to the ground via switches S21 to S2G.

The element seg4a1 is connected to the elements DAS-1a1 to DAS-8a1 and to the ground via switches S31 to S3G. The element seg4a2 is connected to the elements DAS-1a1 to DAS-8a1 and to the ground via switches S41 to S4G. The element seg2a1 is connected to the elements DAS-1a1 to DAS-8a1 and to the ground via switches S51 to S5G. The element seg2a2 is connectedto the elements DAS-1a1 to DAS-8a1 and to the ground via switches S61 to S6G.

The elements seg1a1 to seg1a8 are connected to the elements DAS-1a1 to DAS-8a1 and to the ground via switches S171 to S7G and switches S141 to S14G respectively. The element seg2a3 is connected to the elements DAS-1a1 to DAS-8a1 and to the ground via switches S151 to S15G. The element seg2a4 is connected to the elements DAS-1a1 to DAS-8a1 and to the ground via switches S161 to S16G. The element seg4a3 is connected to the elements DAS-1a1 to DAS-8a1 and to the ground via switches S171 to S17G. The element seg4a4 is connected to the DAS-1a1 to DAS-8a1 and to the ground via switches S181 to S18G.

The elements seg8a3 is connected to the elements DAS-1a1 to DAS-8a1 and to the ground via switches S191 to S19G. The element seg8a4 (twentieth segment) is connected to the elements DAS-1a1 to DAS-8a1 and to the ground via switches S201 to S20G.

Control signal lines that are not shown are routed from a host controller 25 in the system unit 4 to the connection switches S11 to S20G. The connection switches Sll to S20G are mutually-independently turned on or off according to control signals sent from the host controller 25 over the control signal lines. Thus, connection or disconnection of each of the elements sig1a1 to seg1a8, seg2a1 to seg2a4, seg4a1 to seg4a4, and seg8a1 to seg8a4 to or from each of the elements DAS-1a1 to DAS-8a1 and the ground is controlled independently.

The detecting elements belonging to the rows of detecting elements 11a2 to 11a16 constituting the second channel to sixteenth channel are, like those of the row of detecting elements 11a1 constituting the first channel, connected to the associated data acquisition elements DAS-1a2 to DAS-8a2, etc., and DAS-1a16 to DAS-8a16 via connection switches. Each connection switch controls connection or disconnection of each detecting element to or from each data acquisition element of the DAS and the ground according to a control signal sent from the host controller 25.

By the way, the system unit 4 of the X-ray CT scanner 1 includes a data processing unit 26 in which a computer circuit having a CPU and the like is incorporated. The data processing unit 26 retains projection data items of 8 slices acquired by the data acquisition elements of the DAS 21, adds up all the projection data items of the same slice obtained by scanning the subject in multiple directions with the rotation of the gantry 3, and carries out interpolation, correction, or the like on the multi-directional projection data resulting from the addition.

The system unit 4 comprises a memory unit 27 in which data needed for data processing by the data processing unit 26 is stored, a reconstruction unit 28 for reconstructing projection data processed by the data processing unit 26 so as to produce reconstructed image data of 8 slices, a display unit 29 for displaying the reconstructed image data produced by the reconstruction unit 28, an input unit 30 including a keyboard, various switches, mouse, and the like and enabling an operator O to enter various conditions for scanning such as a slice thickness and the number of slice, and an auxiliary memory unit 31 having a large-capacity storage area capable of storing the reconstructed image data produced by the reconstruction unit 28.

The system unit 4 of the X-ray CT scanner 1 includes the host controller 25 in which a computer circuit having a CPU is incorporated. The host controller 25 is connected to the high-voltage generating unit 15, and also connected to the patient couch drive unit, which is not shown, inside the gantry, the gantry drive unit 12, the beam trimmer 14, the group of switches 20, and the DAS 21 respectively over a bus B.

The host controller 25, data processing unit 26, memory unit 27, reconstruction unit 28, display unit 29, input unit 30, and auxiliary memory unit 31 are interconnected over the bus B, and can therefore transfer image data or control data to or from one another over the bus B at a high speed.

In other words, the host controller 25 stores the conditions for scanning such as a slice thickness, which are entered at the input unit 30 by the operator O, in an internal memory. Based on the stored conditions for scanning (or the conditions for scanning designated directly by the operator O in a manual mode), the high-voltage generating unit 15, patient couch drive unit that is not shown, gantry drive unit 12, and beam trimmer 14 are driven while a magnitude of feed of the patient couch 2 in a body-axis direction and a feed speed thereof, a rotating speed of the gantry 3 (X-ray tube 10 and main detector 11) and a rotation pitch thereof, the positions of the edges of a fan beam defined by the beam trimmer 14, and the timing of bombarding X-rays are controlled through the high-voltage generating unit 15, patient couch drive unit, gantry drive unit 12, and beam trimmer 14. Thus, a conical X-ray beam is irradiated in multiple directions to a desired scanned region of the subject P. Transmitted X-rays passing through the scanned region of the subject P are detected as X-ray transmission data by the detecting elements of the main detector 11.

At the same time, the host controller 25 controls connection ore disconnection of each switch of the group of switches 20 on the basis of the conditions for scanning stored in the internal memory (or the conditions for scanning entered in the manual mode) so as to change the connected or disconnected states of the detecting elements of the main detector 11 to the DAS 21. The host controller 25 then combines X-ray transmission data items detected by the detecting elements, and sends resultant data as X-ray transmission data of a plurality of slices that meet the conditions for scanning to the DAS 21.

Next, connection modes for combining X-ray transmission data items using the group of switches 20 in this embodiment will be described. For brevity's sake, only the connections modes for combining X-ray transmission data items detected by the row of detecting elements 11a1 constituting the first channel of the main detector 11, and sending resultant data items to the elements DAS-1a1 to DAS-8a1 are illustrated. Needless to say, the connection modes can also apply to connections between the rows of detecting elements 11a2 to 11a16 constituting the second to sixteenth channels and the elements DAS-1a2 to DAS-8a2 to the elements DAS-1a16 to DAS-8a16.

To begin with, the ways of combining X-ray transmission data items using the group of switches 20 in a data acquisition mode in which data of 8 slices having the same slice thickness is acquired are shown in FIGS. 7 and 8. In FIGS. 7 and 8, a hatched area indicates the range of detecting elements whose detected X-ray transmission data is employed, and a bold line indicates a division of combined X-ray transmission data.

Figure 7A:
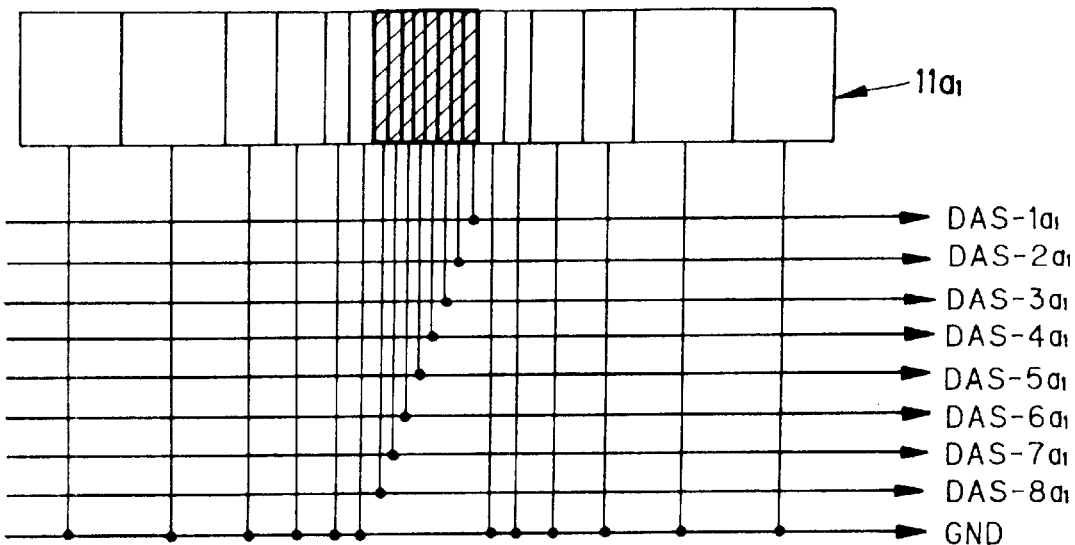
FIGS. 7A and 7B show the way of combining data items in a data acquisition mode in which data of 8 slices having the same pitch relative to adjoining slices is acquired, FIG. 7A showing data acquisition of 8 slices of 1 mm thick and FIG. 7B showing data acquisition of 8 slices of 2 mm thick.

FIG. 7A shows the way of combining X-ray transmission data items using the group of switches 20 in a data acquisition mode in which data of 8 slices having a minimum slice thickness (1 mm) is acquired.

To be more specific, the host controller 25 controls the on or off states of the switches S11 to S20G of the group of switches 20 under the conditions for scanning including the input condition of a slice thickness (1 mm), and combines X-ray transmission data items detected by each row of detecting elements. In other words, the switches S71, S82, S93, S104, S115, S126, S137, and S148 for connecting the elements seg1a1 to seg1a8 to the elements DAS-1a1 to DAS-8a1 are turned on, the other switches S72 to S7G, S8a, S83 to S8G, S91, S92, S94 to S9G, etc., S141 to S147, and S14G are turned off.

The switches S1G, S2G, S19G, and S20G for connecting the elements seg8a1 to seg8a4 to the ground are turned on. The switches S3G, S4G, S17G, and S18G for connecting the elements seg4a1 to seg4a4 to the ground are turned on, and the switches S5G, S6G, S15G, and S16G for connecting the elements seg2a1 to seg2a4 to the ground are turned on. The switches S11 to S18, S21 to S28, S31 to S38, etc., S61 to S68, S151 to S158k, S161 to S168, etc., and S201 to S208 are turned off.

Consequently, X-ray transmission data of 8 slices having a slice thickness of 1 mm can be sent as detected data provided by the row of detecting elements 11a1 constituting the first channel to the elements DAS-1a1 to DAS-8a1.

Figure 7B:
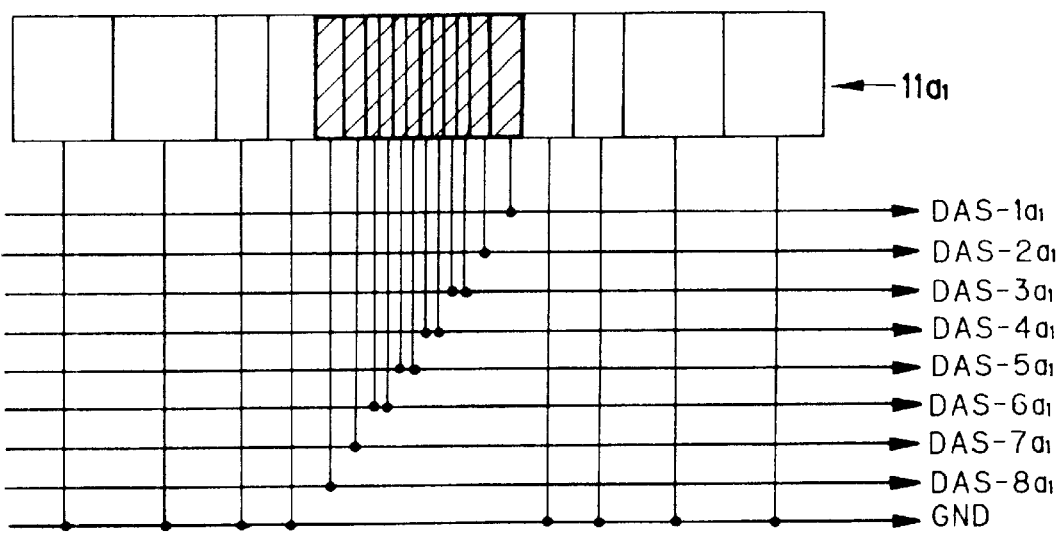

FIG. 7B shows the way of combining X-ray transmission data items using the group of switches 20 in a data acquisition mode in which data of 8 slices having a slice thickness of 2 mm is acquired.

To be more specific, the host controller 25 controls the on or off states of the switches S11 to S20G of the group of switches 20 under the conditions for scanning including the input condition of a slice thickness (2 mm), connects the element seg2a1 to the element DAS-1a1 and the element seg2a2 to the element DAS-2a1, combines the elements seg1a1 and 1a2 and connects them to the element DAS-3a1, combines the elements seg1a3 and seg1a4 and connects them to the DAS-4a1, combines the elements seg1a5 and seg1a6 and connects them to the element DAS-5a1, and combines the elements DAS-6a1. Moreover, the element seg2a3 is connected to the element DAS-7a1, and the element seg2a4 is connected to the element DAS-8a1. All the other elements seg4a1 to seg4a4 and seg8a1 to seg8a4 are grounded.

Consequently, the X-rays which have transmitted a subject are received by the reference and 2 mm-wide segments and converted into electric signals of unequal slice pitches, and then combined by the group of switches. Thus X-ray transmission data of 8 slices having a thickness of 2 mm can be sent as detected data provided by the row of detecting elements 11a1 constituting the first channel to the elements DAS-1a1 to DAS-8a1.

Figure 8A:
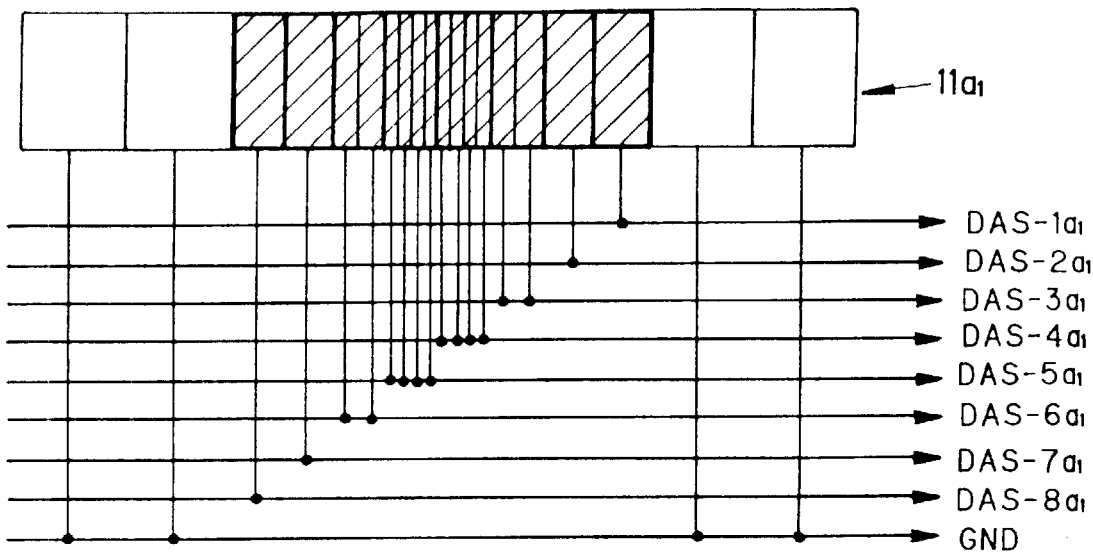
FIGS. 8A and 8B show the way of combining data items in a data acquisition mode in which data of 8 slices having the same pitch relative to adjoining slices is acquired, FIG. 8A showing data acquisition of 8 slices of 4 mm thick and FIG. 8B showing data acquisition of 8 slices of 8 mm thick.

Likewise, in FIG. 8A, the host controller 25 controls the on or off states of the switches S11 to S20G, and thus connects the element seg4a1 to the element DAS-1a1, the element seg4a2 to the element DAS-2a1, the elements seg2a1 and seg2a2 to the element DAS-3a1, the elements seg1a1 and seg1a4 to the element DAS-4a1, the elements seg1a5 to seg1a8 to the element DAS-5a1, the elements seg2a3 and seg2a4 to the element DAS-6a1, the element seg4a3 to the element DAS-7a1, the element seg4a4 to the element DAS-8a1, and the elements seg8a1 to seg8a4 to the ground respectively.

Consequently, the X-rays which have transmitted a subject are received by the reference, 2 mm-wide and 4 mm-wide segments and converted into electric signals of unequal slice pitches, and then combined by the group of switches. Thus X-ray transmission data of 8 slices having a thickness of 4 mm can be sent as detected data provided by row of detecting elements 11a1 constituting the first channel to the elements DAS-1a1 to DAS-8a1.

Figure 8B:
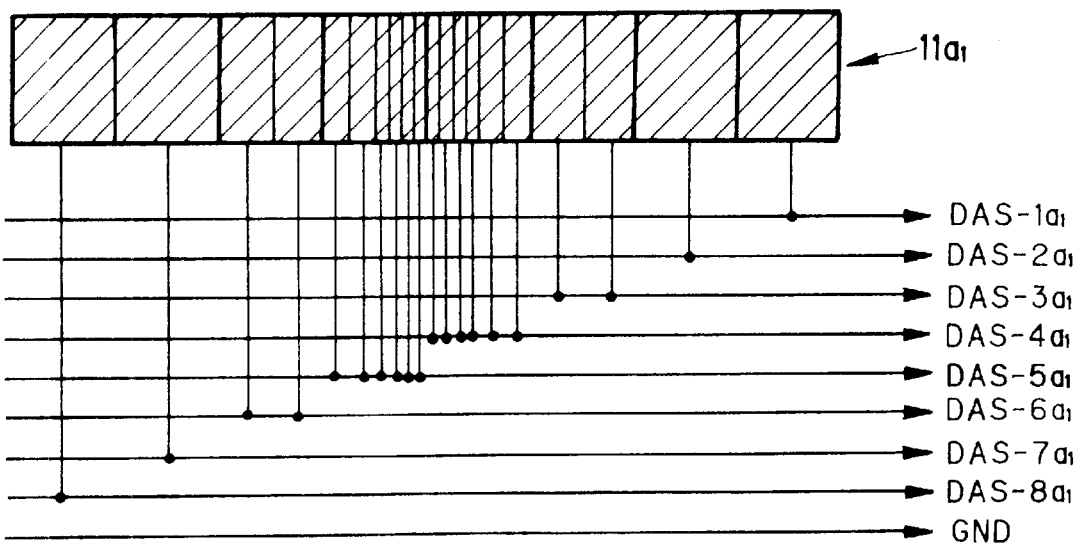

In FIG. 8B, the on or off states of the switches S11 to S20G are controlled in order to connect the element seg8a1 to the element DAS-1a1, the element seg8a2 to the element DAS-2a1, the elements seg4a1 and seg4a2 to the element DAS-3a1, the elements seg2a1 and seg2a2 and the elements seg1a1 to seg1a4 to the element DAS-4a1, the elements seg1a5 to seg1a8 and the elements seg2a3 and seg2a4 to the element DAS-5a1, the elements seg4a3 and seg4a4 to the element DAS-6a1, the element seg8a3 to the element DAS-7a1, and the element seg8a4 to the element DAS-8a1.

Consequently, the X-rays which have transmitted a subject are received by the reference, 2 mm-wide, 4 mm-wide, and 8 mm-wide segments and converted into electric signals of unequal slice pitches, and then combined by the group of switches. Thus X-ray transmission data of 8 slices having a slice thickness of 8 mm can be sent as detected data provided by the row of detecting elements 11a1 constituting the first channel to the elements DAS-1a1 to DAS-8a1.

As mentioned above, according to this embodiment, in a data acquisition mode in which X-ray transmission data of 8 slices having the same slice thickness is acquired, the slice thickness can be continuously doubled to be 2 mm, 4 mm, and 8 mm.

Any of the slice thickness is selected according to the conditions for scanning (including the condition of a slice thickness) by automatically controlling connection or disconnection of the group of switches 20 under the control of the host controller 25 on the basis of a slice thickness included in the conditions for scanning designated by the operator O.

Specifically, according to this embodiment, X-ray transmission data of 8 slices having a minimum slice thickness (1 mm) can be acquired under the designated condition of a slice thickness. Based on projection data stemming from the acquired X-ray transmission data of 8 slices, the reconstruction unit 28 carries out reconstruction. This results in reconstructed images of 8 slices having high resolving power (resolution) in the slice-thickness direction. Moreover, X-ray transmission data of a wide scanned region (64 mm) defined with 8 slices having a slice thickness of, for example, 8 mm can be acquired under the designated condition of a slice thickness. The reconstruction unit 28 then carries out image reconstruction on the basis of projection data stemming from the acquired X-ray transmission data. Consequently, a reconstructed image of the wide range in the slice-thickness (body-axis) direction can be produced. In this embodiment, therefore, both high resolution in the slice-thickness direction and a wide scanned region therein can be realized.

Moreover, according to this embodiment, when projection data of 8 slices having the same slice thickness is acquired, a value to be set as the slice thickness can be doubled to be 1 mm, 2 mm, 4 mm, and 8 mm according to the designated condition of a slice thickness. Moreover, the condition of a slice thickness can be designated arbitrarily by the operator O at the time of designating the conditions for scanning or in a manual mode. Consequently, the freedom in designating a slice thickness can be increased greatly, and image diagnosis can be achieved efficiently according to a diagnostic region. In this configuration, it is also possible that projection data of 8 slices different in thickness from each other are acquired, not limited to the same slice thickness.

Still, the configuration is characterized in that X-rays are converted to fluorescent signals by the scintillators $16a1 \ldots 16a1$ to $16a4 \ldots 16a4$ whose slice thicknesses are the same, and the fluorescent signals are converted to output detection signals of unequal slice thicknesses corresponding to unequal segment pitches by the photodiodes $17a1 \ldots 17a1$ to $17a4 \ldots 17a4$ having unequal element pitches also corresponding to unequal slice thicknesses. Namely, with the slice thicknesses of the scintillators $16a1 \ldots 16a1$ to $16a4 \ldots 16a4$ being kept in the same value, detection signals corresponding to unequal slice thicknesses are outputted, thus eliminating irregularities in sensitivity (i.e., bias in sensitivity distributions) that occur where the scintillators of the detecting elements are different in slice thickness from each other.

Figure 9:
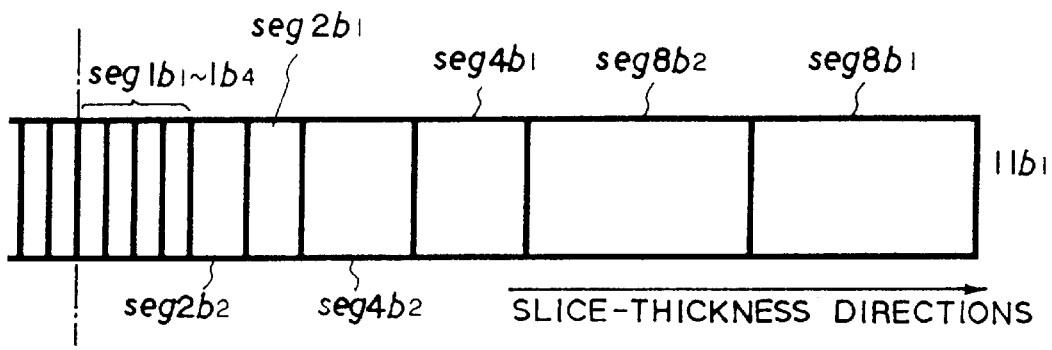
FIG. 9 is a view representing the structure of a row of detecting elements of a main detector, the element row being configured in unequal pitches in slice thickness of a main detector.

The foregoing advantage will be explained in detail. FIG. 9 illustrates a row of detecting elements 11b1, which corresponds to the row of detecting elements 11a1 and expresses a one-sided half of a row of detecting elements (reference segments seg1b1 to seg1b8, 2 mm-wide segments seg2b1 to seg2b4, 4 mm-wide segments seg4b1 to seg4b4, and 8 mm-wide segments seg8b1 to seg8b4) the scintillators and photodiodes of which are unequal in slice thickness.

Figure 10A:
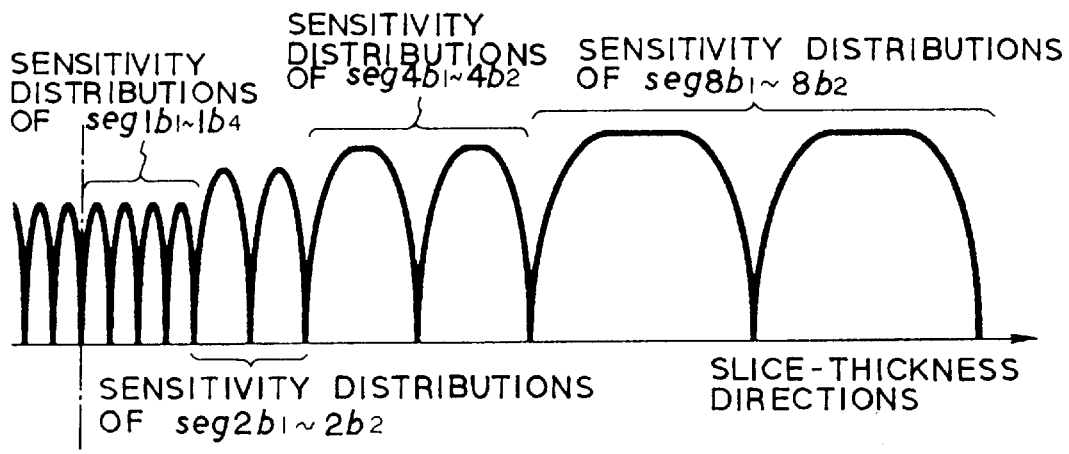
FIG. 10A shows an example of sensitivity distributions for segments constituted by the row of the detecting elements shown by FIG. 9.
Figure 10B:
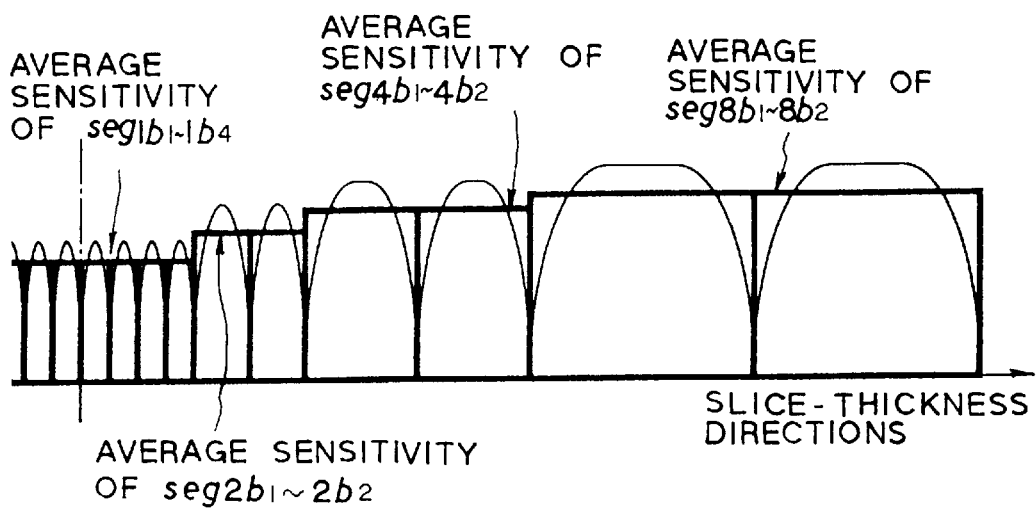
FIG. 10B shows an example of average sensitivities for segments constituted by the row of the detecting elements shown by FIG. 9.

As described before, the sensitivity distribution of each segment depends on the slice thickness of a scintillator. Hence, as shown in FIGS. 10A and 10B, the reference segments seg1b1 to seg1b4 (and seg1b5 to seg1b8) whose scintillators are shorter in slice thickness have lower sensitivities (average sensitivities) than other surrounding segments such as 8 mm-wide segments.

Figure 11:
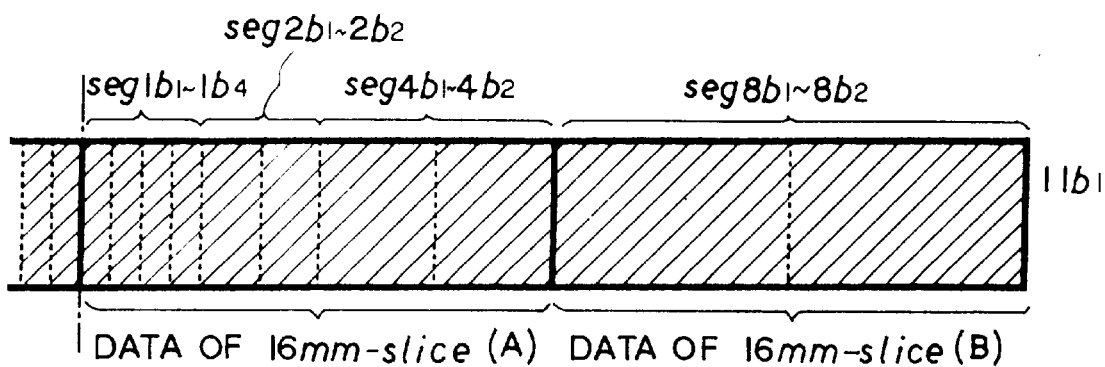
FIG. 11 is a conceptual view for producing data of slices of 16 mm thick by combining the detecting elements shown in FIG. 9.
Figure 12A:
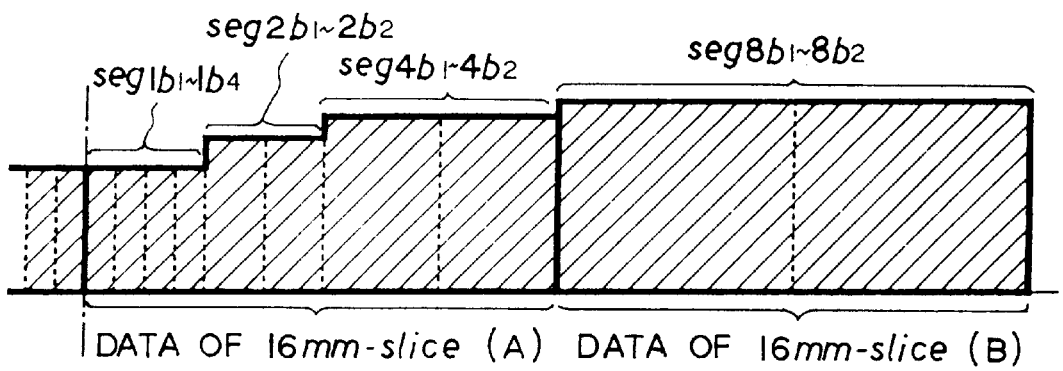
FIG. 12A shows sensitivity distributions of slice data of 16 mm thickness produced by combining signals detected from different slices in thickness and sensitivity distributions of slice data of 16 mm thickness produced by combining signals detected from slices in the same thickness.

Assume that, for example, by ON/OFF control of the switching elements of the switch group 20, segments seg1b1 to seg1b4, seg2b1 and seg2b2, and seg4b1 and seg4b2 are combined to provide X-ray transmission data of 16 mm-slice (16 mm-slice (A) as in FIG. 11) and segments seg8b1 and seg8b2 are combined to provide X-ray transmission data of 16 mm-slice (16 mm-slice (B) as in FIG. 11). In such case, even when the X-ray transmission data are provided to form the same slice thickness, the X-ray transmission data (16 mm-slice (A) in FIG. 11) provided by combining segments of different slice thicknesses have irregularities in sensitivity distributions, as shown in FIG. 12A. On one hand, the X-ray transmission data (16 mm-slice (B) in FIG. 11) provided by combining segments of the same slice thickness represent a flat sensitivity distribution, as shown in FIG. 12A.

Figure 12B:
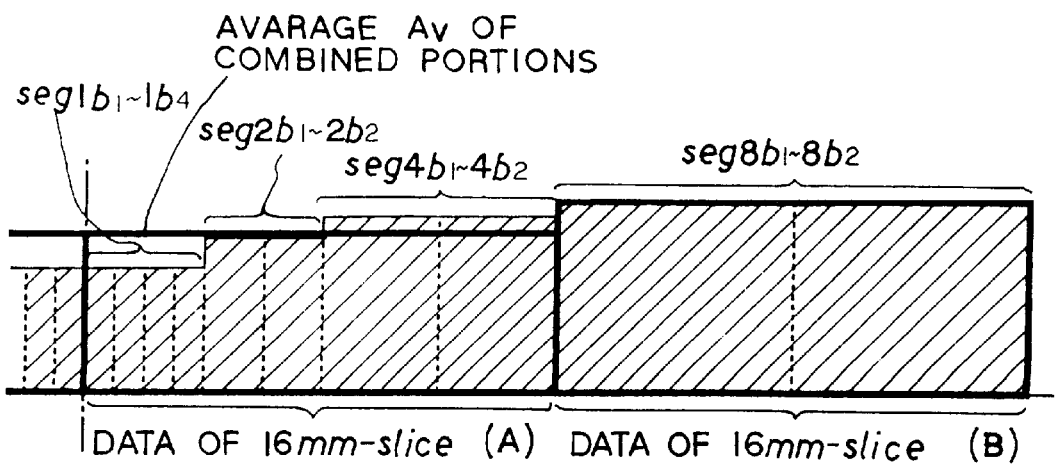
FIG. 12B shows averages of the combined sensitivity distributions shown in FIG. 12A.

In conventional CT scanners, when the X-ray transmission data of 16 mm-slice (A) are processed with some data processing method such as sensitivity correction, there remains only one method that an average Av over the combined segments is determined, as shown in FIG. 12B and used for such data processing. This results in that, as clearly understood from FIG. 12B, the weight for the transmission data through the segments seg4b1 and seg4b2 having a larger slice thickness gets larger compared with that through the segments segb1 to segb4 having a smaller slice thickness.

Such differences in the weight caused by differences in slice thicknesses changes (increased or decreased) depending on a difference between the direction of a subject and the slice-thickness direction, thus outputs from the detector being changed.

Furthermore, since such differences due to differences in slice thicknesses generate in the remaining rows (channels) of detecting elements and the degrees of their differences changes with each other, the whole detector outputs different detection values every row of detecting elements. This has been a main factor for artifacts which might appear in transmission images.

However, in the present configuration, as shown in FIG. 4, while the scintillator $16a1 \ldots 16a1$ to $16a4 \ldots 16a4$ of the segments have the same slice thickness, detection signals are outputted in the form of unequal slice thicknesses and the outputted signals are combined to create X-ray transmission data of a plurality of slices. Consequently, the foregoing irregularities (differences) in sensitivity distributions caused by differences in slice thicknesses can well be eliminated, and artifacts resultant from the irregularities can be suppressed.

In the foregoing embodiment, although the widths of all the scintillators of the segments are set to the same quantity in agreement with a slice thickness (in this case, 1 mm) of the reference segments, the present invention is not confined to such configuration. Alternatively, by way of example, the slice thickness set to the same quantity can be set to quantities produced by dividing a slice thickness (for example, 1 mm) of the reference segments by a common divisor for an acquired slice thickness (for example, 8 mm); the quantities are ½ mm, ¼ mm, and ⅛ mm in this example.

Still, when influence of differences in sensitivity distributions is relatively small, the configuration in which scintillators are set to the same slice thickness can be partly applied to each row of detecting elements, not to all thereof.

Second Embodiment

Figure 13:
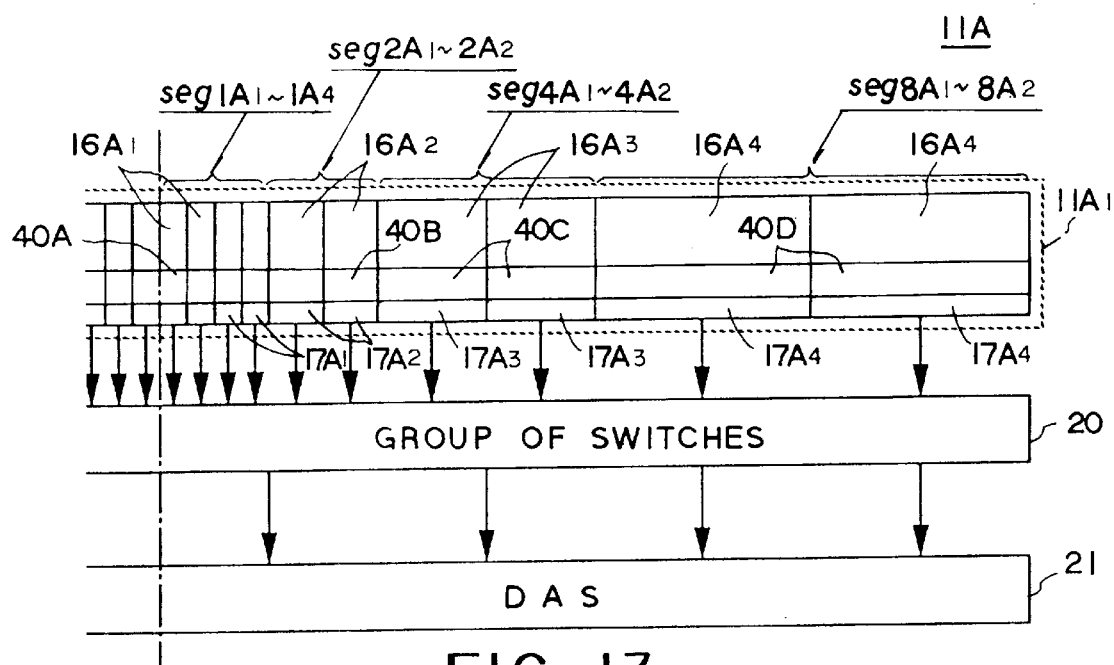
FIG. 13 shows the internal structure of a row of detecting elements constituting the first channel of a main detector according to a second embodiment of the present invention.

FIG. 13 illustrates the internal structure of a row 11A1 (to 11A16) of detecting elements for each channel of a main detector 11A according to a second embodiment, which has unequal element pitches. In FIG. 13, only half of the row 11A1 for the first channel is representatively illustrated, and the remaining half is symmetrically made and not shown. Also the remaining rows for the second to sixteenth channels have the same internal structure. The other components and performance thereof other than the main detector 11A are the same or similar as or to those in the first embodiment, thus explanation for those is omitted. (This way of explanation will be applied to further embodiments subsequent to the second embodiment.)

The row of detecting elements 11A1 for the first channel comprises reference segments seg1A1 to seg1A4 (and seg1A5 to seg1A8) each having a single scintillator 16A1. Each scintillator 16A1 has an X-ray incidence area the size of which is set in agreement with a slice pitch (1 mm in this embodiment) of the reference segments in the slice-thickness direction.

Each scintillator 16A1 has a fluorescent output surface on which an optical filter 40A1 transmitting fluorescent light is disposed via a jointing member such as adhesive or optical compound. On the fluorescence output surface of the optical filter 40A is provided an optical sensor (specifically, photodiode) 17A1, arranged via a jointing member, for receiving fluorescent signals. Each photodiode 17A1 has an active area set in agreement with the slice pitch (1 mm) of each reference segment and receives through the active area a fluorescent signal generated by the scintillator 16A1 to convert it to a corresponding electric signal to be outputted.

Each of 2 mm-wide segments seg2A1 and seg2A2 (and seg2A3 and seg2A4) has a single schintillator 16A2 disposed along the slice-thickness direction in the detector 11A. Each scintillator 16A2 has an X-ray incidence area the size of which is set to a slice thickness in agreement with a slice pitch (2 mm in this embodiment) of each 2 mm-wide segments.

Each scintillator 16A2 has a fluorescent output surface on which an optical filter 40A1 transmitting fluorescent light is disposed via a jointing member. On the fluorescence output surface of the optical filter 40B is provided an optical sensor (specifically, photodiode) 17A1, arranged via a jointing member, for receiving fluorescent signals. Each photodiode 17A1 has an active area set in agreement with the slice pitch (2 mm) of each 2 mm-wide segment and receives through the active area a fluorescent signal generated by the scintillator 16A1 to convert it to a corresponding electric signal to be outputted.

Each of 4 mm-wide segments seg4A1 and seg4A2 (and seg4A3 and seg4A4) has a single schintillator 16A3 disposed along the slice-thickness direction in the detector 11A. Each scintillator 16A2 has an X-ray incidence area the size of which is set to a slice thickness in agreement with a slice pitch (4 mm in this embodiment) of each 4 mm-wide segments.

Each scintillator 16A3 has a fluorescent output surface on which an optical filter 40A1 transmitting fluorescent light is disposed via a jointing member. On the fluorescence output surface of the optical filter 40C is provided an optical sensor (specifically, photodiode) 17A1, arranged via a jointing member, for receiving fluorescent signals. Each photodiode 17A1 has an active area set in agreement with the slice pitch (4 mm) of each 4 mm-wide segment and receives through the active area a fluorescent signal generated by the scintillator 16A1 to convert it to a corresponding electric signal to be outputted.

Each of 8 mm-wide segments seg8A1 and seg8A2 (and seg8A3 and seg8A4) has a single schintillator 16A4 disposed along the slice-thickness direction in the detector 11A. Each scintillator 16A2 has an X-ray incidence area the size of which is set to a slice thickness in agreement with a slice pitch (8 mm in this embodiment) of each 8 mm-wide segments.

Each scintillator 16A4 has a fluorescent output surface on which an optical filter 40A1 transmitting fluorescent light is disposed by a jointing member. On the fluorescence output surface of the optical filter 40D is provided an optical sensor (specifically, photodiode) 17A1, arranged via a jointing member, for receiving fluorescent signals. Each photodiode 17A1 has an active area set in agreement with the slice pitch (8 mm) of each 8 mm-wide segment and receives through the active area a fluorescent signal generated by the scintillator 16A1 to convert it to a corresponding electric signal to be outputted.

Additionally, the optical filters 40A, 40B, 40C, and 40D of the reference, 2 mm-wide, 4 mm-wide, and 8 mm-wide segments are different in light transmittance from each other.

Of these, optical filters having larger transmittances are disposed in segments of less light sensitivities (i.e., light amounts outputted per unit light-receiving area), which have relatively narrower slice-thicknesses. In contrast, optical filters having lesser transmittances are disposed in segments of greater light sensitivities, which have relatively wider slice-thicknesses. In other words, finally-detected sensitivities, electric signal amounts per unit size (i.e., width of slice-thickness) outputted from the photodiodes 17A1 . . . 17A1 to 17A4 . . . 174A of the segments, are adjusted depending on the slice thicknesses to realize the same value or approximately the same value.

Therefore, as described in the first embodiment, each of the reference, 2 mm-wide, 4 mm-wide, and 8 mm-wide segments is able to detect X-rays as electric signals in agreement with its slice-thickness forming the unequal slice pitches, and the detected electric signals are combined by the switch group 20 to form X-ray transmittance data of a plurality of slices sent to the DAS 21.

In this acquisition, the sensitivity distributions of the photodiodes 17A1 . . . 17A1 to 17A4 . . . 17A4 of the segments are adjusted to be uniform by the optical filters 40A to 40D having different transmittances from each other and being inserted every segment, thereby, like the first embodiment, eliminating irregularities in sensitivity distribution caused by differences in slice-thickness and surppressing artifacts in images resultant from the irregularities in sensitivity distribution.

In the second embodiment, although an optical filters is inserted between the photodiode and scintillator of each segment and the sensitivity of each segment is adjusted by the transmittances of the optical filters, the present invention is not restricted to such structure.

As an example, instead of using optical filters, the light transmittance of the jointing member, such as adhesive or optical compound, used to directly jointing the scintillator and photodiode in each segment, can be changed segment by segment such that the detection sensitivities of the segments become uniform. Further the optical filters can be replaced with ND filters for decreasing amounts of light transmission from the scintillator to photodiode without affecting its energy distribution.

Still, as a variation for the optical filters, light-transmitting members may be inserted into the scintillator and photodiode of each segment, the members being formed, for example, a liquid crystal panel capable of changing its light transmittance by the external control.

Figure 14:
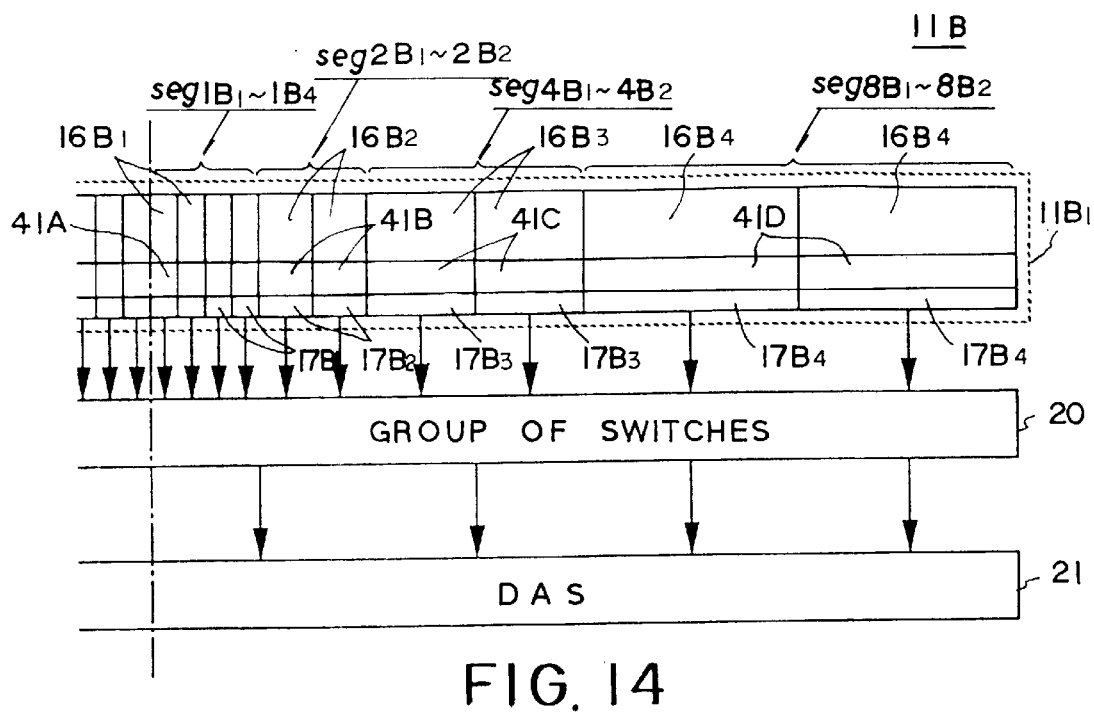
FIG. 14 shows the internal structure of a row of detecting elements constituting the first channel of a main detector according to a variant of the second embodiment of the present invention.

FIG. 14 shows one such example, in which a main detector 11B having a plurality of rows of detecting elements 11B1 to 11B16 each forming an unequal element pitch system (only one row 11B1 is partially shown).

The configuration shown in FIG. 14 includes light-transmitting members 41A . . . 41A to 41D and 41D each light-transmittance of which is settable to a desired amount by the external control (e.g. control of applied voltages), which are inserted instead of the optical filters in FIG. 13. In such a case, the host controller 25 may be used for an external controller. Specifically, inserted between a scintillator 16B1 and a photodiode 17B1 of each of the reference segments seg1B1 to seg1B4 (and seg1B4 to seg1B8) is a light-transmitting member 41A having a light-transmittance of υ10, inserted between a scintillator 16B2 and a photodiode 17B2 of each of the 2 mm-wide segments seg2B1 and seg2B2 (and seg2B3 and seg2B4) is a light-transmitting member 41B of a light transmittance υ11. Likewise, a light-transmitting member 41C of a light transmittance υ12 and a light-transmitting member 41D of a light transmittance υ13 are inserted into each of 4 mm-wide segments and each of 8 mm-wide segments, respectively. The remaining structure and components are constructed in the same or similar way as or to the first and second embodiments.

The light transmittances υ10 to υ13 are set in the following manner. After having assembled the detector 11B, each segment of each detecting element row is measured in terms of its sensitivity, and on the basis of the measured results, the light transmittance υ10 (to υ13) of the member 41A (to 41P) is controlled (for example, applied-voltage controlled) so that all the sensitivity distributions become flat over the segments. Basically, the control of the light transmittances is carried out depending on the size of the segments. However, if necessary, the control is possible to be done by the unit of segment, where irregularities in sensitivity between segments belonging to the same slice thickness can suitably be corrected. In addition to the control of sensitivity of the segments solely, the light transmittances υ10 to υ13 can be controlled in accordance with scan conditions including the thickness of X-ray beams transmitted through a subject P or conditions including combining switches of the DAS 21. In this way, the light transmittances υ10 to υ13 can be controlled depending on various parameters in a basic condition that sensitivity given to X-ray transmission data created by the combination is kept uniform at the data acquiring elements of the DAS 21.

As described above, the sensitivity distribution of an output from each segment of the reference, 2 mm-wide, 4 mm-wide, and 8 mm-wide segments or the sensitivity distributions of outputs combined by the switch group 20 can be kept uniformly, thereby eliminating irregularities in sensitivity distribution caused by differences in slice-thickness and suppressing artifacts in images caused by those irregularities.

Third Embodiments

Figure 15:
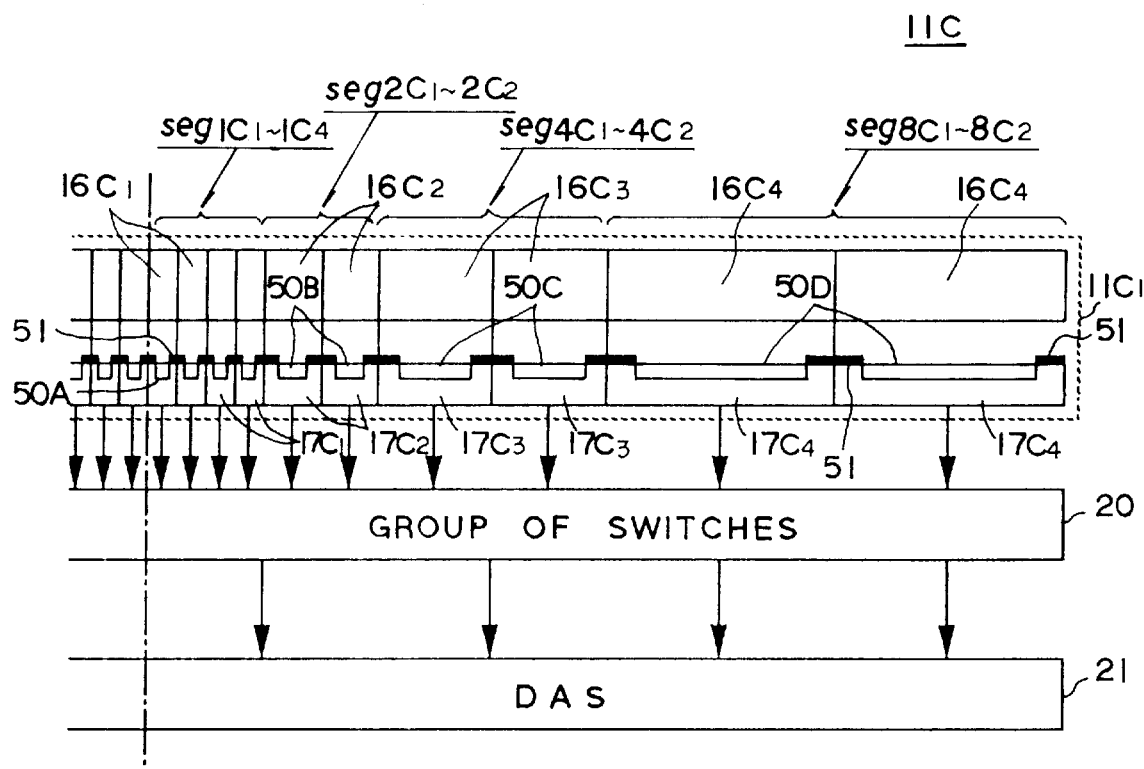
FIG. 15 shows the internal structure of a row of detecting elements constituting the first channel of a main detector according to a third embodiment of the present invention.

FIG. 15 shows the internal structure of a row of detecting elements 11C1 (to 11C6) corresponding to each channel of a main detector 11C according to a third embodiment of the present invention, which is structured on the basis of an unequal element pitch manner.

Each segment of the reference, 2 mm-wide, 4 mm-wide and 8 mm-wide segments of the row 11C1 has a scintillator 16C1 ( . . . 16C1 to 16C4 . . . 16C4) and a photodiode 17C1 ( . . . 17C1 to 17C4 . . . 17C4) both of which are constructed in an unequal element pitch structure in agreement with required segment sizes (slice thicknesses) as in the second embodiment. Also the group of switches 20 is used to combine detected signals of unequal slice thicknesses provided from the photodiodes 17C1 . . . 17C1 to 17C4 and 17C4, so that combined X-ray transmission data of a plurality of slices are sent to the DAS 21.

Normally the size of the active area of each photodiode is determined by the slice thickness of each segment. In the embodiment, however, the size of the active area is determined to create a desired detection sensitivity of each segment. In other words, the active area serves as a parameter for controlling detection sensitivities.

Specifically, in the detecting element row 11C1 of the first channel, an active area 50A of each of the reference segments seg1C1 to seg1C4 (and seg1C5 to seg1C8), an active area 50B of each of the 2 mm-wide segments seg2C1 and seg2C2 (and seg2C3 and seg2C4), an active area 50C of each of the 4 mm-wide segments seg4C1 and seg4C2 (and seg4C3 and seg4C4), and an active area 50D of each of the 8 mm-wide segments seg8C1 and seg8C2 (and seg8C3 and seg8C4) are set such that detection sensitivities become the same value or thereabout through all the segments. The detection sensitivity is defined as amounts per unit size of the slice thickness provided by electric signals outputted from each photodiode.

In the case of the active area 50D of seg8C1, for example, its active area 50D is partly covered by a light-absorbing member 51 placed on the edges of the area in the slice-thickness direction. By increasing or reducing areas covered by the light-absorbing member 51 permits an effective area of the predetermined active area to be adjusted. The remaining segments have the same structure concerning the light-absorbing member 51.

As in the first and second embodiments, each of the reference, 2 mm-wide, 4 mm-wide, and 8 mm-wide segments is able to detect X-rays as electric signals in agreement with its slice thickness forming the unequal slice pitches, and the detected electric signals are combined by the switch group 20 to form X-ray transmittance data of a plurality of slices sent to the DAS 21.

As described above, thanks to the structure that the sizes of the active areas 50A . . . 50A to 50D and 50D of the photodiodes 17C1 . . . 17C1 to 17C4 and 17C4 are determined dependently on the detection sensitivity of each segment, differences in the sensitivities of segments (scintillators) caused from differences in slice thickness are suitably cancelled out by differences in amounts of light received by the photodiodes through the area-adjusted active areas. Thus the output signals from the photodiodes 17C1 . . . 17C1 to 17C4 and 17C4 are the same or approximately the same in sensitivity. In other words, detection sensitivities of all the segments are uniformed or substantially uniformed.

As a result, irregularities in sensitivity distribution caused by differences in slice thickness are remarkably diminished, thereby properly suppressing artifacts which might appear in reconstructed images due to the irregularities.

In the foregoing configuration, the light-absorbing member 51 covers light-receiving areas other than a specified active areas to adjust the sizes of the whole active area. The present invention can provide various variants in this aspect. For example, for the purpose of preventing electric charges generated in light-receiving areas other than the specified active areas from being included into the output signal of the photodiode, the light-receiving areas other than the specified active area may have ground (GND) electrodes connected to the ground.

Further, by way of example, the light-absorbing member or ground electrode may be positioned at either one edge of each specified active area in the slice-thickness direction, instead of positioning it at both the edges thereof in the slice-thickness direction.

Still further, instead of adjusting the size of the active area, the structure itself of the active area of the pn-junction portion can be changed segment by segment; for example, the thickness of the pn-junction portion or the thickness of a protective layer thereof can be controlled every segment so that differences in sensitivity of the scintillators 16C1 . . . 16C1 to 16C4 and 16C4 due to differences in slice thickness are properly reduced to become a uniform value.

Fourth Embodiment

Figure 16:
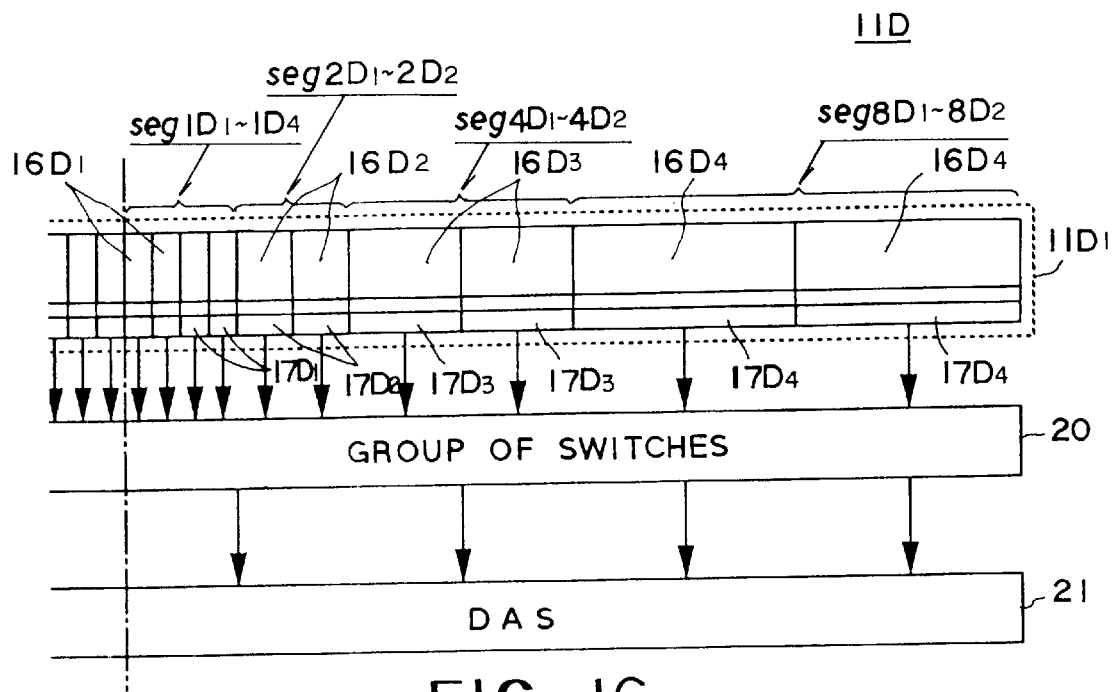
FIG. 16 shows the internal structure of a row of detecting elements constituting the first channel of a main detector according to a variant of a fourth embodiment of the present invention.

FIG. 16 shows the internal structure of a row of detecting elements 11D1 that is a representative of the detecting element rows 11D1 to 11D16 constituting a main detector 11D of the embodiment. All the element rows adopt unequal element pitches.

In the element row 11D1 for the first channel, each row of scintillators 16D1 . . . 16D1 to 16D4 . . . 16D4 and photodiodes 17D1 . . . 17D1 to 17D4 . . . 17D4 of the segments is constructed in an unequal element pitch manner, like the second embodiment. The group of switches 20 is arranged to combine signals detected from the photodiodes on the basis of the unequal slice thickness manner into X-ray transmission data of a plurality of slices (multi-slice), which are then sent to the DAS 21.

In the above configuration, manufacturing conditions for each of the scintillators 16D1 . . . 16D1 to 16D4 . . . 16D4 are changed every scintillator. The manufacturing conditions includes temperatures, pressures, and duration time for solidifying fluorescent powder, or, sintering conditions for ceramic scintillators.

Controlling the manufacturing conditions for the scintillators enables the variable setting of their transparency values (i.e., light transmittance). Hence determining the transparency values of the scintillators on the basis of the manufacturing conditions employed as parameters in a manner that output signals from each of the photodiodes have a uniform sensitivity distribution appropriately eliminates irregularities in sensitivity distribution caused from differences in slice thicknesses of the scintillators, and suppressing most artifacts in images.

Alternatively, in the invention, the light-emitting efficiencies themselves of the scintillators can be adjusted every slice thickness (segment size). This also enables to eliminate irregularities in sensitivity distribution caused by differences in slice thickness. For example, the light-emitting efficiency can be adjusted by altering components (their kinds or content ratios) of a fluorescent member of which scintillators are made.

Fifth Embodiment

Figure 17:
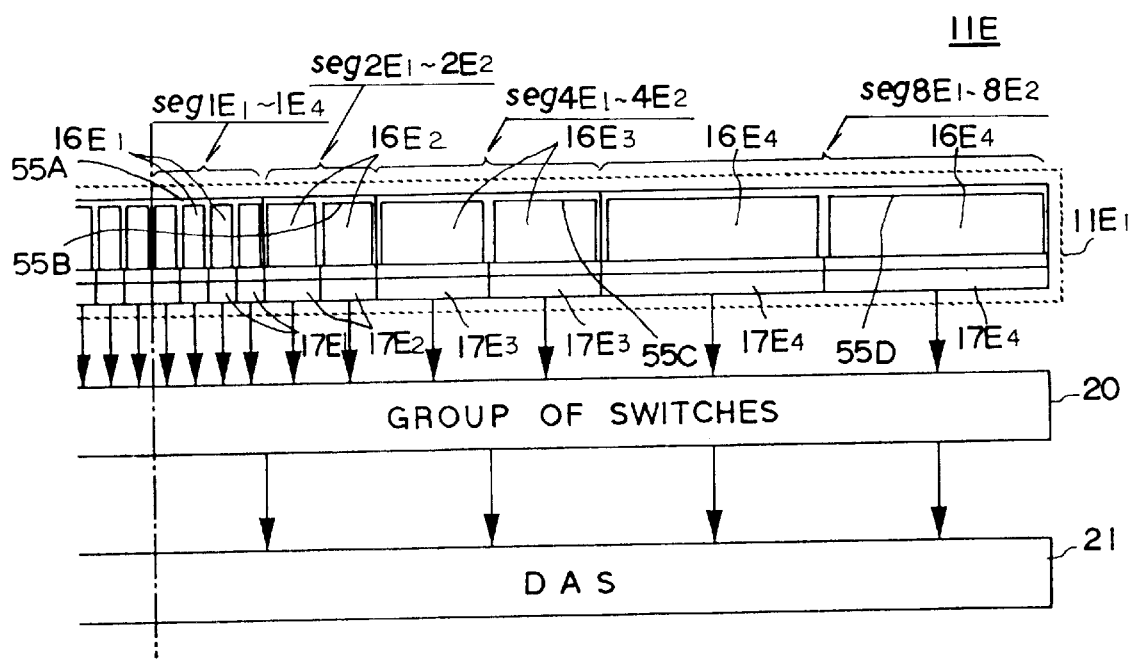
FIG. 17 shows the internal structure of a row of detecting elements constituting the first channel of a main detector according to a fifth embodiment of the present invention.

FIG. 17 shows the internal structure of a row of detecting elements 11E1 that is a representative of the detecting element rows 11E1 to 11E16 constituting amain detector 11E of the embodiment. All the element rows adopt unequal element pitches.

In the element row 11E1 for the first channel, each row of scintillators 16E1 . . . 16E1 to 16E4 . . . 16E4 and photodiodes 17E1 . . . 17E1 to 17E4 . . . 17E4 of the segments is constructed in an unequal element pitch manner, like the second embodiment. The group of switches 20 is arranged to combine signals detected from the photodiodes on the basis of the unequal slice thickness manner into X-ray transmission data of a plurality of slices, which are then sent to the DAS 21.

Particularly in the above configuration, the reflection rates rA to rD of light-reflecting members 55A . . . 55A to 55D . . . 55D, which are individually arranged in a layer on an X-ray incidence surface and sides in the channel and slice-thickness directions of each of the scintillators 16E1 . . . 16E1 to 16E4 . . . 16E4, are changed in accordance with segment sizes (i.e., slice thicknesses).

Changes in the reflection rates rA to rD of the light-reflecting members lead to changes in incidence efficiencies of fluorescent light reaching the photodiodes 17E . . . 17E1 to 17E4 . . . 17E4 via the scintillators 16E1 . . . 16E1 to 16E4 . . . 16E4. This changes the sensitivity distributions of the photodiodes. Hence, it is possible to set the reflection rates rA to rD in a manner that an output signal from each photodiode have an equal sensitivity distribution to others. Therefore, as in the first to fourth embodiments, irregularities in sensitivity distribution of each segment caused by differences in slice thickness can be suitably eliminated, and artifacts of images can be well suppressed.

In the embodiment, instead of controlling the reflection rates, materials themselves or the thickness itself of the light-reflecting member can be changed in the same way as above. Still the surface itself of each scintillator can be changed into various kinds of surface (such as mirror-finished surface or diffusing surface), thereby controlling incidence efficiencies of fluorescent light impinging to the photodiodes.

Sixth Embodiment

Figure 18:
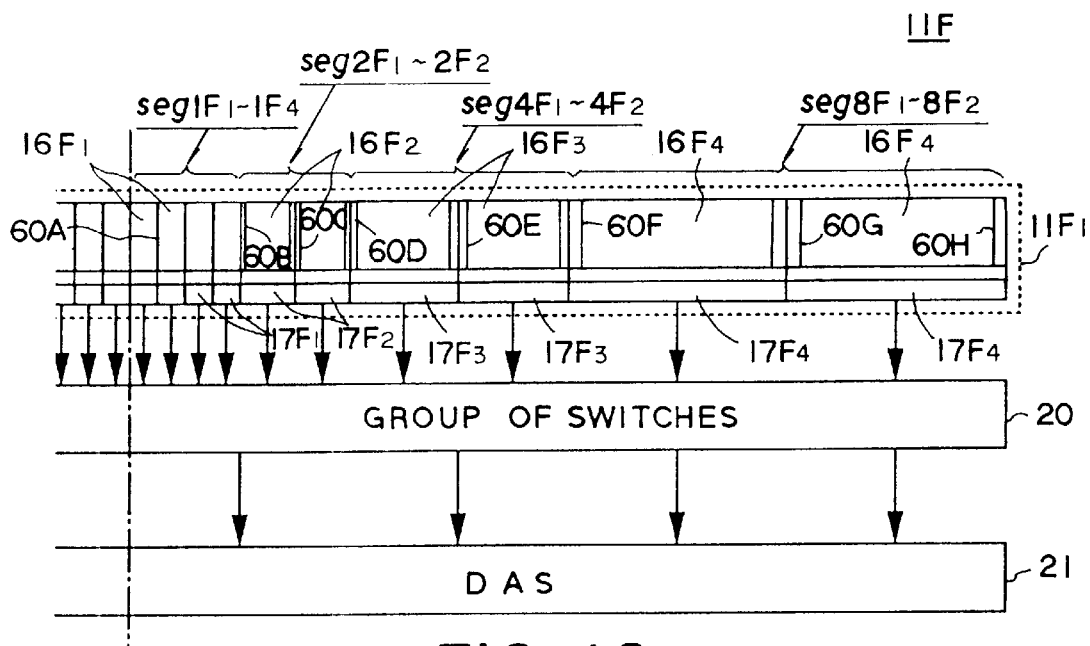
FIG. 18 shows the internal structure of a row of detecting elements constituting the first channel of a main detector according to a variant of a sixth embodiment of the present invention.

FIG. 18 shows the internal structure of a row of detecting elements 11F1 that is a representative of the detecting element rows 11F1 to 11F16 constituting a main detector 11F of the embodiment. All the element rows adopt unequal element pitches.

In the element row 11F1 for the first channel, each row of scintillators 16F1 . . . 16F1 to 16F4 . . . 16F4 and photodiodes 17F1 . . . 17F1 to 17F4 . . . 17F4 of the segments is constructed in an unequal element pitch manner, like the second embodiment. The group of switches 20 is arranged to combine signals detected from the photodiodes on the basis of the unequal slice thickness manner into X-ray transmission data of a plurality of slices, which are then sent to the DAS 21.

Particularly in the embodiment, separators inserted between adjoining segments are changed in thickness, thereby controlling the sizes of the scintillators (i.e., the sizes of X-ray incidence areas or the thicknesses in the slice direction) for realizing uniformity in detection sensitivities.

Assume that a separator 60A (thickness=wA) is inserted between two of the reference segments, a separator 60B (thickness=wB) between the end-positioned reference and 2 mm-wide segments, a separator 60C (thickness=wC) between two of the 2 mm-wide segments, a separator 60D (thickness=wD) between the end-positioned 2 mm- and 4 mm-wide segments, a separator 60E (thickness=wE) between two of the 4 mm-segments, a separator 60F (thickness=wF) between the end-positioned 4 mm- and 8 mm-wide segments, a separator 60G (thickness=wG) between two of the 8 mm-segments, and a separator 60H (thickness=wH) adjacently to one-sided 8 mm-segment. Changing the thickness wA to wH of the separators allows the X-ray incidence efficiencies of the scintillators to be changed, thus changing the sensitivity distributions of detection signals provided from the photodiodes via the scintillators.

Setting of the thicknesses wA to wH of the separators 60A to 60H in a manner such that an output signal of each corresponding photodiode to each segment has a uniform sensitivity distribution with the others provides the similar advantages to the first to fifth embodiments.

Other variants can be used instead of adjusting the thickness of the separator. For example, an X-ray filter having adjustable X-ray transmittances can be placed on or above the X-ray incidence surface (in the X-ray tube side) of each scintillator, so that amounts of X-rays impinging into the scintillator can solely be adjusted by control of the X-ray transmittances to achieve the uniformity of detection sensitivities.

Seventh Embodiment

Figure 19:
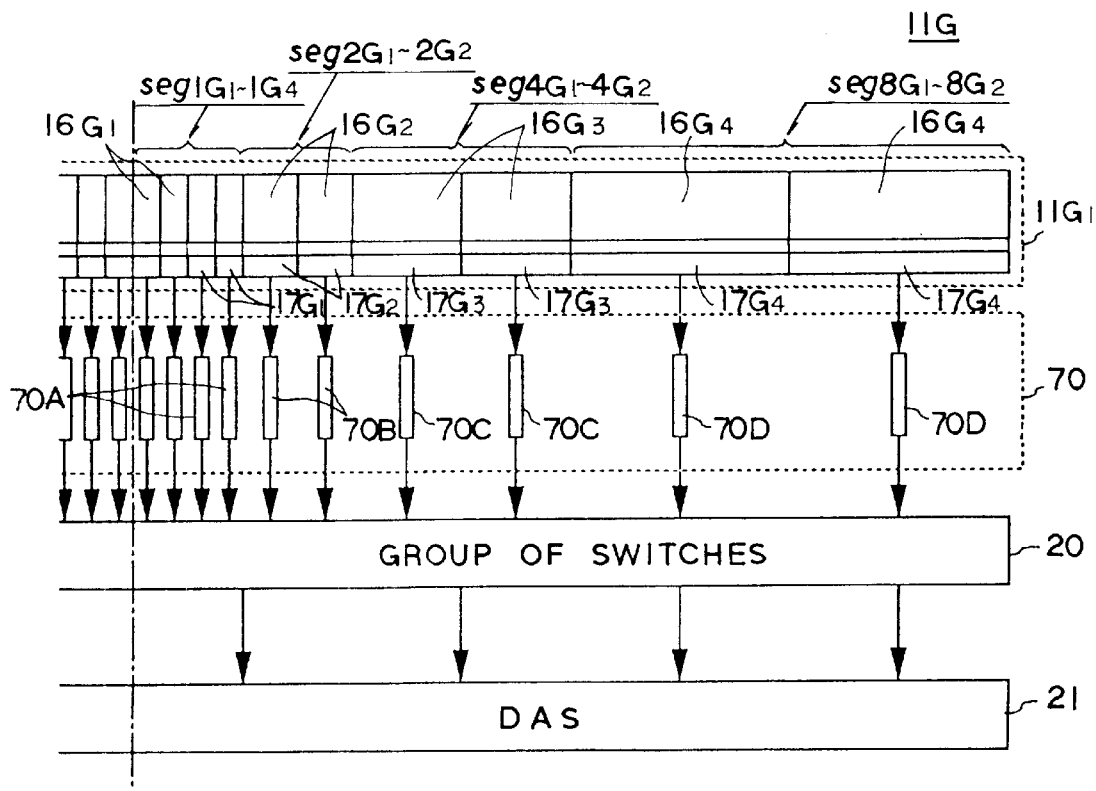
FIG. 19 shows the internal structure of a row of detecting elements constituting the first channel of a main detector according to a seventh embodiment of the present invention.

FIG. 19 shows the internal structure of a row of detecting elements 11G1 that is a representative of the detecting element rows 11G1 to 11G16 constituting a main detector 11G of the embodiment. All the element rows adopt unequal element pitches.

In the element row 11G1 for the first channel, each row of scintillators 16G1 . . . 16G1 to 16G4 . . . 16G4 and photodiodes 17G1 . . . 17G1 to 17G4 . . . 17G4 of the segments is constructed in an unequal element pitch manner, like the second embodiment. The group of switches 20 is arranged to combine signals detected from the photodiodes on the basis of the unequal slice thickness manner into X-ray transmission data of a plurality of slices, which are then sent to the DAS 21.

Particularly, between the element row 11Gl and the switch group 20 is provided a group of gain-variable amplifier 70 for adjusting sensitivities of the segments segment by segment.

More specifically, a amplifier 70A is connected between each segment of the reference segments and the switch group 20 for controlling the sensitivity of the segment. Likewise, amplifiers 70B, 70C and 70D are connected between the 2 mm-, 4 mm-, and 8 mm-wide segments and the switch group 20.

Adjusting, for example, the gains of the amplifiers 70A . . . 70A to 70D . . . 70D segment by segment enables control of sensitivity distributions output signals detected every segment group. This sensitivity can also be done every detecting element. In the case of the latter, irregularities in sensitivity which are caused at each element of the same-size segment group can also be corrected. In this case, in addition to sensitivity control based on the sensitivity distribution of each segment, the sensitivity control depending on the amplifiers may be done based on scan conditions such as the thickness of X-ray beams that have transmitted a subject P or based on manners to combine the switches of the DAS 21. In this way, the sensitivity-adjusting amplifiers can be controlled using a wide range of parameters. If any parameter is used in the control, it is basically enough for the control that the sensitivity distributions of combined and outputted X-ray transmission data become uniform at the data acquiring elements of the DAS 21.

Therefore, also in this embodiment, the sensitivity distributions of the output signals for each same-size segment group (or the sensitivity distributions of X-ray transmittance data combined by the group of switches 20) become uniform with each other. This also almost eliminates the irregularities in sensitivity distribution described before, and suppresses artifacts in images.

In the first to seventh embodiments X-ray transmission data detected by the main detector 11, in which a total of 20 segments whose widths range from 1 mm to 8 mm are arranged to constitute each channel, is acquired as projection data by the DAS 21 that includes data acquisition elements numbering a multiple of 8 slices. The rules on the relationship between the number of data acquisition elements of the DAS and the number of segments belonging to a row of detecting elements is not limited to such configuration.

For setting a slice thickness, which is realized by combining segments using the group of switches 20, to a value that is $2^k$ (1, 2, 4, 8, etc.) times as large as a reference slice thickness, the DAS 21 should preferably include data acquisition elements numbering a product of "4 by n slices (where n is a natural number)" per row of detecting elements constituting each channel. The segments belonging to each row of detecting elements of the main detector 11 are arranged in such a way that reference segments numbering a product of 4 by n are laid out in the center, segments numbering a product of 2 by n in total and each having a width that is twice as large as the width of each reference segment are laid out on both outer sides of the reference segments by arranging n segments on each side, segments numbering a product of 2 by n in total and each having a width that is twice as large as the width of each of the preceding segments (four times as large as the width of each reference segment) are laid out on both sides of the preceding segments by arranging n segments on each side, and so on.

Eighth Embodiment

Figure 20:
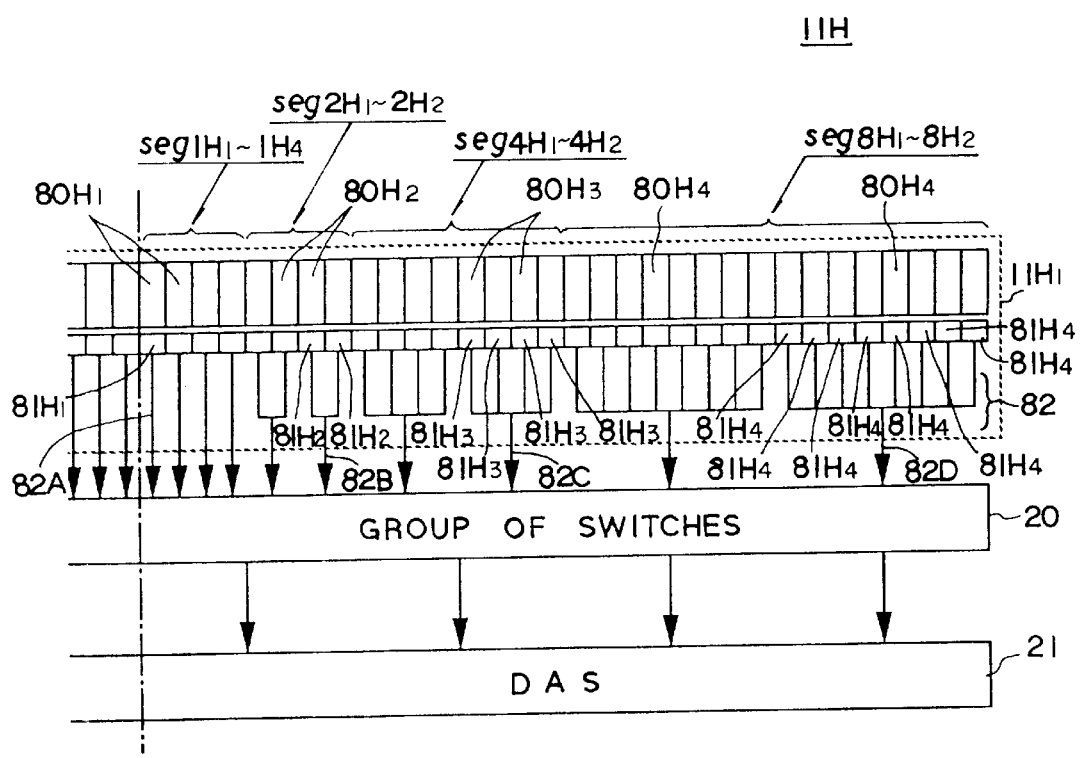
FIG. 20 shows the internal structure of a row of detecting elements constituting the first channel of a main detector according to an eighth embodiment of the present invention.

This embodiment employs amain two-dimensional X-ray detector in which each row of detecting elements thereof is disposed in equal size pitches in the slice-thickness direction and that generates detection signals based on unequal slice pitches, although the foregoing embodiments have employed the unequal slice pitches that are gradually broadened from the center to both the ends in each row of detecting elements in the slice-thickness direction FIG. 20 shows the internal structure of a main X-ray detector 11H, in which representatively illustrated is a row of detecting elements 11H1 for the first channel of the detector 11H.

In the row 11H1, eight segments constituting a group of reference segments seg1H1 to seg1H4 (and seg1H5 to seg1H8 not shown) for reference slice thickness consists of a minimum slice thickness (1 mm) of segment, respectively. Also the row 11H1 includes groups of 2 mm-wide segments seg2H1 and seg2H2 (and seg2H3 and seg2H4 not shown) for 2 mm-wide slice thickness, 4 mm-wide segments seg4H1 and seg4H2 (and seg4H3 and seg4H4 not shown) for 4 mm-wide slice thickness, and 8 mm-wide segments seg8H1 and seg8H2 (and seg8H3 and seg8H4 not shown) for 8 mm-wide slice thickness segments constituting each of the three group of segments also consists of a segment equals I slice thickness (1 mm) the segment constituting the group of reference segments.

Specifically, each reference segment seg1H1 (to seg1H8) has a scintillator 80H1 whose slice thickness is the reference slice thickness (1 mm) and a photodiode 81H1, connected with the fluorescence output surface of the scintillator, whose active area has the reference slice thickness. The same slice thickness is also applied to a scintillator 80H2 and photodiode 81H2 of each 2 mm-wide segment seg2H1 (to seg2H4), a scintillator 80H3 and photodiode 81H3 of each 4 mm-wide segment seg4H1 (to seg4H4), and a scintillator 80H4 and photodiode 81H4 of each 8 mm-wide segment seg8H1 (to seg8H4).

Further, data-combining leads 82 . . . 82 are provided for electrically combining detection signals provided from the active areas of the photodiodes 81H1 . . . 81H1 to 81H4 . . . 81H4 into detection signals of a plurality of slices of unequal pitches, the electrically combined detection signals being sent to the group of switches.

More specifically, the active areas of the photodiodes 81H1 belonging to the reference segments seg1H1 to seg1H8 are electrically connected to the group of switches directly via leads 82A . . . 82A, respectively. Hence detection signals from the photodiodes 81H1 are sent to, as signals of 1 mm slice thickness, the group of switches 20 via the leads 82A.

For each of the 2 mm-wide segments seg2H1 to seg2H8, the active areas of adjacent and paired two photodiodes 81H2 and 81H2 are electrically combined and connected to the group of switches via leads 82B . . . 82B. hence detection signals from each of the pairs of two photodiodes 81H2 and 81H2 are sent to the group of switches 20 as signals of 2 mm slice thickness thanks to the combination.

For each of the 4 mm-wide segments seg4H1 to seg4H4, the active areas of adjacent and grouped four photodiodes 81H3 . . . 81H3 are electrically combined and connected to the group of switches via leads 82C . . . 82C. Hence detection signals from each of the groups of four photodiodes 81H3 . . . 81H3 are sent to the group of switches 20 as signals of 4 mm slice thickness thanks to the combination.

For each of the 8 mm-wide segments seg8H1 to seg8H4, the active areas of adjacent and grouped eight photodiodes 81H4 . . . 81H4 are electrically combined and connected to the group of switches via leads 82D . . . 82D. Hence detection signals from each of the groups of eight photodiodes 81H4 . . . 81H4 are sent to the group of switches 20 as signals of 8 mm slice thickness thanks to the combination.

Although the X-ray CT scanners of the foregoing various embodiments have been configured to employ only one factor for equalizing the sensitivity distributions over the segments of each main detector, such configurations are mere examples of the present invention. Alternatively, a plurality of factors for equalizing those can combinedly be included into a single main detector of an X-ray CT scanner. Such inclusion can be realized in a wide range of combinations, and one example will be described by the following tenth embodiment.

Ninth Embodiment

This embodiment employs a main two-dimensional detector configured in the same element structure as the eighth embodiment, in which each row of detecting elements constituting each channel consists of detecting elements disposed in equal element pitches. On the basis of this element configuration, detection signals of the foregoing unequal segment (slice) pitches are produced by the detector.

Figure 21:
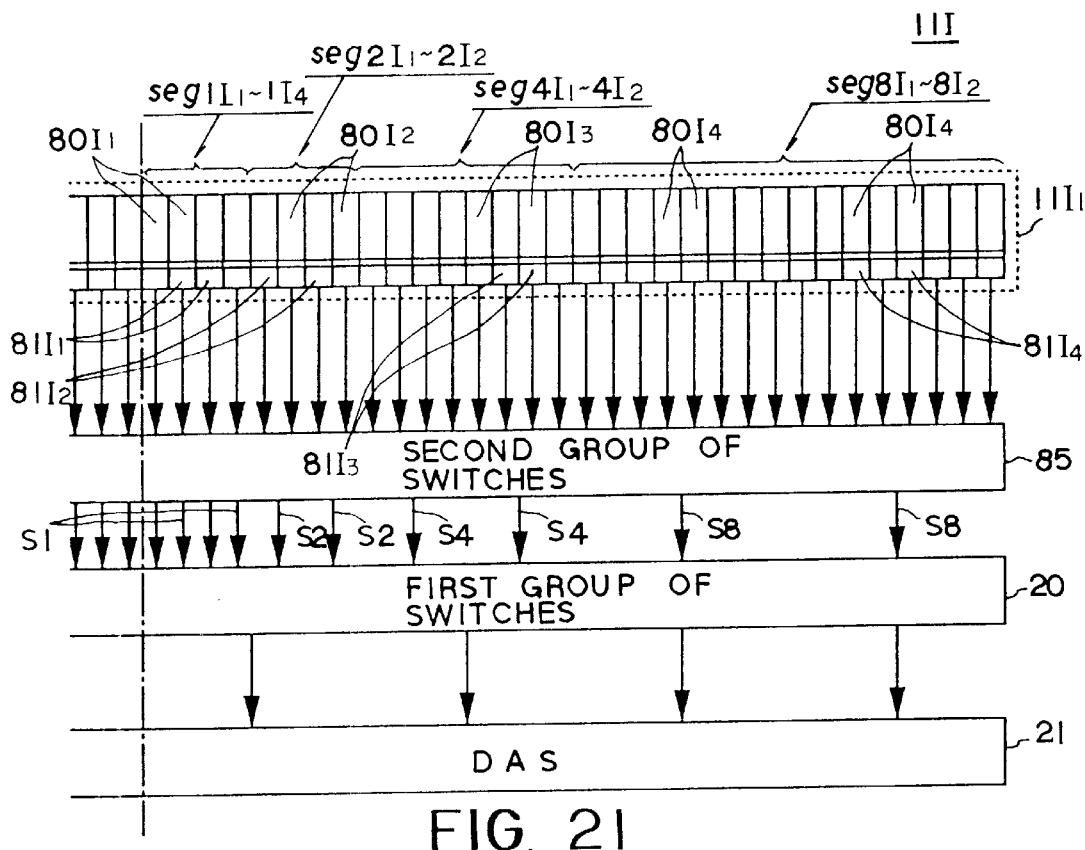
FIG. 21 shows the internal structure of a row of detecting elements constituting the first channel of a main detector according to a ninth embodiment of the present invention, a first group of switches connected to a DAS, and a second group of switches placed between the detecting elements and the first group of switches.

FIG. 21 shows the internal structure of a main detector 11I according to the embodiment. The main detector 11I1, which is representatively shown, is provided with groups of reference segments seg1i1 to seg1I8, 2 mm-wide segments seg2I1 to seg2I4, 4 mm-wide segments seg4I1 to seg4I4, and 8 mm-wide segments seg8I1 to seg8I4. Each segment is constituted by one or more than one detecting elements having a minimum slice thickness referred to as the reference thickness of 1 mm, as described in the eighth embodiment. As a result, the detecting elements of the minimum slice thickness are disposed side by side in equal element pitches. That is, the thickness of a scintillator 80I1 and the active area of a photodiode 81I1 belonging to each reference segment seg1I1 (to seg1I8), that of a scintillator 80I2 and that a photodiode 81I2 constituting in pairs each 2 mm-wide segment seg2I1 (to seg2I4), that of a scintillator 80I3 and that of a photodiode 81I3 constituting in a group each 4 mm-wide segment seg4I1 (to seg4I4), and that of a scintillator 80I4 and that of a photodiode 81I4 constituting in a group each 8 mm-wide segment seg8I1 (to seg8I4) are all equally formed into the minimum thickness of 1 mm in the slice-thickness direction.

A second group of switches 85 is arranged between the group of switches 20 in order to combine signals of the equal slice thicknesses corresponding to the equal element pitches (1 mm) detected by the active areas of the photodiodes 81I1 . . . 81I1 to 81I4 . . . 81I4 and to provide the group of switches 20 the combined detection signals of the unequal slice thicknesses corresponding to the unequal segment pitches.

Specifically, the group of switches 85 is constructed such that an output signal detected by each photodiode 81I1 of each reference segment is provided, without any combination of signals, as a detection signal of 1 mm slice thickness to the group of switches 20. In contrast, for the 2 mm-wide segments, the group of switches 25 includes circuitry that output signals detected by paired two photodiodes 81I2 are provided as a combined detection signal S2 of 2 mm slice thickness to the group of switches 20. For the 4 mm- and 8 mm-wide segments, the group of switches includes the similar circuitry to the above. Namely, output signals detected by grouped four photodiodes 81I3 belonging to each 4 mm-wide segment are combined into a single detection signal S4 to be sent to the group of switches 20. Output signals detected by grouped eight photodiodes 81I4 belonging to each 8 mm-wide segment are combined into a single detection signal S8 to be sent to the group of switches 20.

The provided detection signals S1, S2, S4, and S8 of unequal slice thicknesses defined by the unequal segment pitches are further combined into X-ray transmission data of a plurality of slices (multi-slices) to be sent to the DAS 21.

Accordingly, with the sizes of the core elements (i.e., scintillators and photodiodes (active areas)) constituting all the segments kept at the same size in the slice-thickness direction, the detection signals according to unequal slice thicknesses can be provided. Like the embodiments described before, irregularities resulting from differences in slice thicknesses can be kept markedly low, and therefore artifacts due to the irregularities can also be suppressed low.

Figure 22:
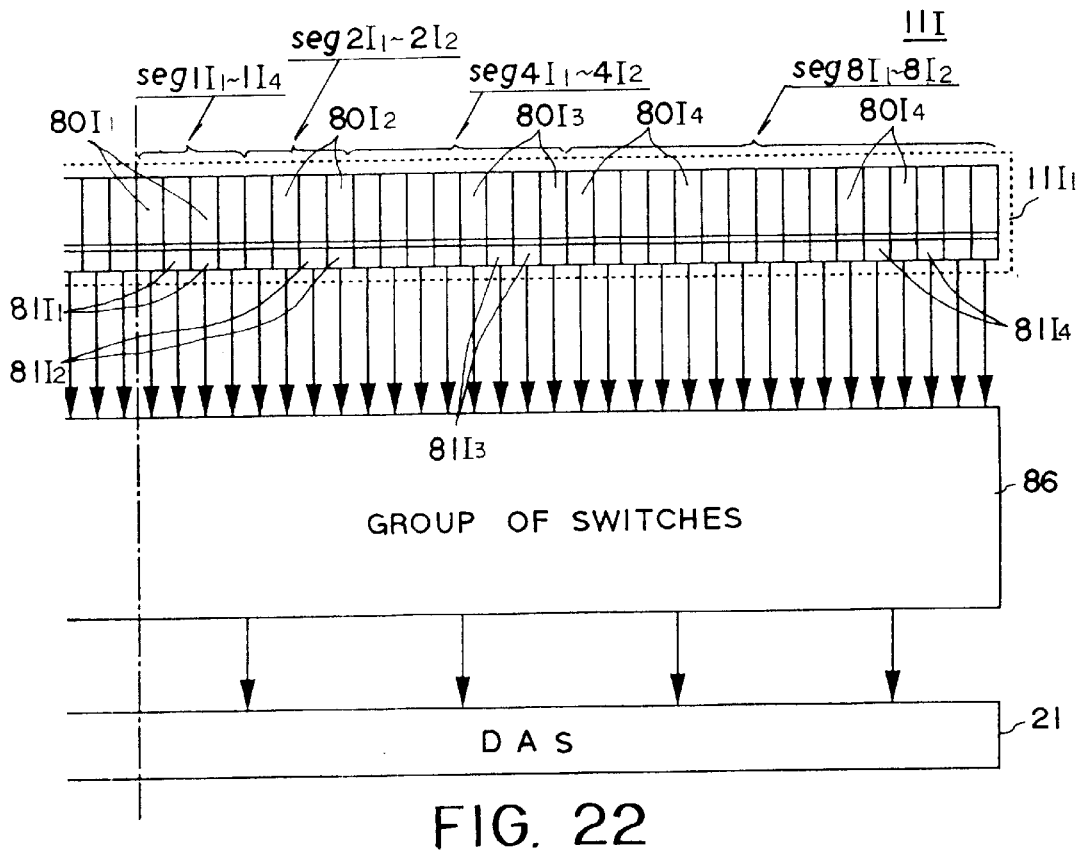
FIG. 22 shows the internal structure of a row of detecting elements constituting the first channel of a main detector according to a variant of the ninth embodiment of the present invention, and a group of switches placed between the detecting elements and a DAS.
Figure 23:
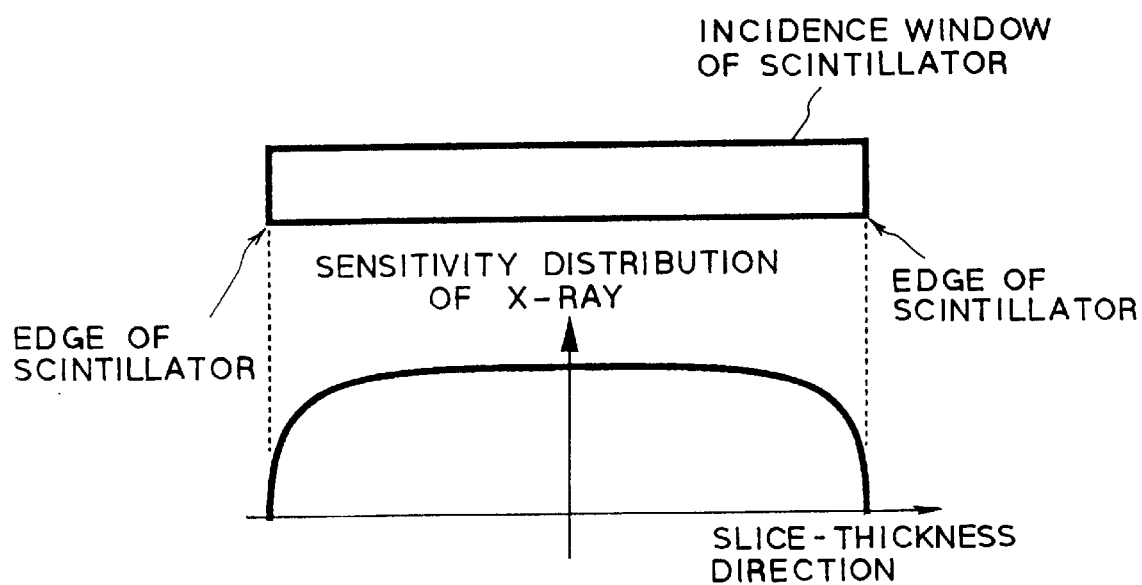
FIG. 23 is a sensitivity distribution to show changes in the sensitivity curve along the edge portions of a scintillator.

A variant for the ninth embodiment is shown in FIG. 22, in which a group of switches 86 is placed between the main detector 11I and the DAS 21. The group of switches 86 itself is in charge of switching carried out by both the groups of switches 85 and 20 shown in FIG. 21.

In the eight to ninth embodiments X-ray transmission data detected by the main detector 11, in which a total of 20 segments are arranged to constitute each channel, is acquired as projection data by the DAS 21 that includes data acquisition elements numbering a multiple of 8 slices. The rules on the relationship between the number of data acquisition elements of the DAS and the number of segments belonging to a row of detecting elements is not limited to such configuration.

For setting a slice thickness, which is realized by combining segments using the groups or group of switches, to a value that is $2^k$ (1, 2, 4, 8, etc.) times as large as a reference slice thickness, the DAS 21 should preferably include data acquisition elements numbering a product of "4 by n slices (where n is a natural number)" per row of detecting elements constituting each channel. The segments belonging to each row of detecting elements of the main detector 11 are arranged in such a way that reference segments numbering a product of 4 by n are laid out in the center, 2 mm-wide segments numbering a product of 4 by in total and each including the core elements each having a width that is the same as the width of each reference segment are laid out on both outer sides of the reference segments by arranging 2·n segments on each side, 4 mm-wide segments numbering a product 8 by n in total and each including the core elements each having a width that is the same as the width of each reference segment are laid out on both sides of the preceding segments by arranging 4·n segments on each side, and so on.

In the foregoing embodiments, instead of using the scintillation detectors as the main detector, any two-dimensional X-ray detector may be used, provided that optical or electric signals are generated in response to the incidence of X-rays and the detection sensitivity in the slice-thickness direction varies with changed slice thicknesses of segments.

Tenth Embodiment

Figure 24:
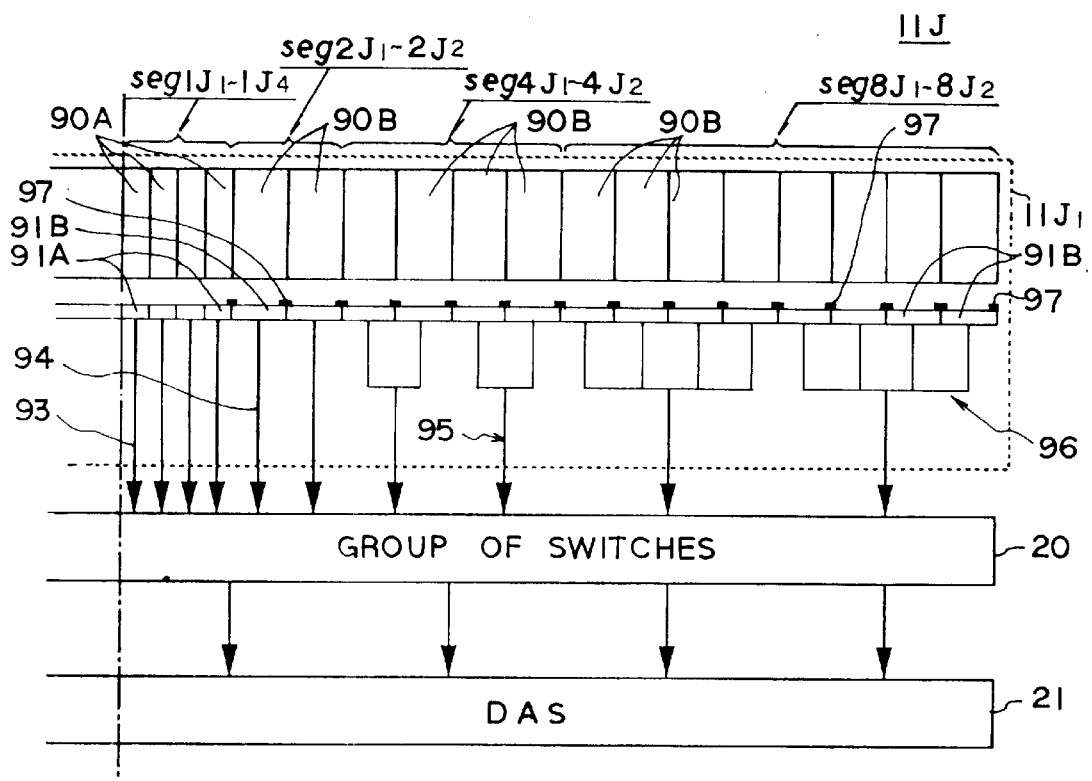
FIG. 24 shows the internal structure of a row of detecting elements constituting the first channel of a main detector according to a tenth embodiment of the present invention.

As in the same way as the foregoing embodiments, FIG. 24 shows the internal structure of one row of detecting elements 11J1 in a main X-ray detector 11J. The detector 11J comprises a plurality of rows of detecting elements for a plurality of channels. The row 11j1 is a representative of all the rows which have the same structure and is for the first channel, for example.

In the row of detecting elements 11j1, there are provided a plurality of four groups of segments. Though the symmetrical left-hand-side half of the row 11J1 is not shown therein, the row includes a group of reference segments seg1J1 to seg1J8, a group of 2 mm-wide segments seg2J1 to seg2J4, a group of 4 mm-wide segments seg4J1 to seg4J4, and a group of 8 mm-wide segments seg8J1 to seg8J4, as in the foregoing embodiments.

Each reference segment seg1J1 (to seg1J8) is provided with a scintillator 90A of a predetermined minimum thickness (1 mm) in the slice-thickness direction and a photodiode 91A of the same slice-directional thickness placed in the face of the fluorescent output surface of the scintillator 90A. Each photodiode 91A is electrically connected via a sole lead 93 to the group of switches 20 to send its output to the switch group.

Each 2 mm-wide segment seg2J1 (to seg2J4) is provided with a scintillator 90B having a double-sized slice thickness (2 mm) of the minimum one and a photodiode 91B of the same slice-directional thickness placed in the face of the fluorescent output surface of the scintillator 91B. Each photodiode 90B is electrically connected via a sole lead 94 to the group of switches 20.

For each 4 mm-wide segment seg4J1 (to seg4J4) and each 8 mm-wide segment seg8J1 (to seg8J4), the same element unit of the 2 mm-wide scintillator 90B and 2 mm-wide photodiode 91B as each 2 mm-wide segment is adopted. For making each of the 4 mm-wide segments, the outputs of paired two photodiodes 90B are electrically combined and connected by a combining lead 95 to the group of switches 20. Also for making each of the 8 mm-wide segments, the similar wiring is done. Namely, the outputs of grouped four photodiodes 90B are electrically combined and connected by a combining lead 96 to the group of switches 20.

As a result, for each entire row, eight reference segments are produced based on the reference slice thickness of 1 mm, and four segments for each of the 2 mm-, 4 mm-, and 8 mm-wide segments are produced based on the 2 mm-wide slice thickness. Segment pitches over the entire row 11J1 are therefore unequal, but segment pitches over the groups of the 2 mm-, 4 mm-, and 8 mm-wide segments are equal. For realizing unequal slice pitches of 2 mm-, 4 mm-, and 8 mm-wide, the leads 94 and 95 are used based on the same concept described in the eighth embodiment. Using the combination of the same size of segment pitches and the combining leads 95 and 96 and connecting leads 94 enables to output X-ray transmittance data of unequal slice pitches of 2 mm-, 4 mm-, and 8 mm-wide with the sensitivity distributions of their data being equalized.

In addition, to equalize the sensitivity distributions between the reference segments and 2 mm-wide or wider segments, the concept described in the third embodiment is adopted. Specifically, as shown in FIG. 24, light-reflecting members 97 covers both the slice-directional edges of an active area of each photodiodes 91B, which belong to only the 2 mm-, 4 mm-, and 8 mm-wide segment groups. Covering with the light-reflecting members 97, which is made of light-masking resin, for example, can adequately reduce the effective light-receiving area in the active area for sensitivity adjustment. The light-reflecting members can be placed on either of both the edges in the channel direction of the active area of each photodiode. Hence, a difference in sensitivity between the reference segments and the 2 mm- or wider segments can be diminished almost completely.

Consequently, the entire row 11J1 can be uniformly adjusted in sensitivity for its finally-output detection signals constituting X-ray transmittance data, thereby providing the main detector having an entirely uniformed sensitivity distribution.

As described above, detection signals of equal element pitches outputted from each segment are sent through the leads 82A, 82B, 82C, and 82D to the group of switches 20 as signals of unequal segment pitches (i.e., unequal slice thicknesses). And, by the group of switches 20, the detection signals of unequal segment pitches are further combined into X-ray transmittance data of multi-slice of a specified slice thickness and sent to the DAS 21.

The same slice thickness defined by the reference segments can therefore be used in all the segments, while detection signals of unequal slice thicknesses can be outputted. As a result, the similar or equivalent advantages to the embodiments described before are obtained.

Although various specific constructions have been given for the present invention, it is to be understood that these are for illustrative purpose only. Various modifications and adaptations will be readily apparent to those skilled in the art without departing from the substance or scope of the invention. Accordingly, it is intended that the invention be limited only by the spirit and scope of the claims appended hereto.

What we claim is:

1. An X-ray CT scanner for obtaining a computed tomography (CT) image of a subject, the scanner comprising:
   means for radiating an X-ray fan beam spreading in a slice-thickness direction;
   means for scanning the subject with the X-ray fan beam;
   means for detecting the X-ray fan beam transmitted through the subject with a detecting element array including a plurality of X-ray detecting elements two-dimensionally disposed in the slice-thickness direction and a channel direction orthogonal to the slice-thickness direction, the X-ray detecting elements of the array being classified in the slice-thickness direction into a plurality of groups each including at least one channel-directional line of X-ray detecting elements each of which has an aperture to receive the X-ray fan beam, the aperture being changed in width in the slice-thickness direction on a basis of an unequal element pitch when viewed group by group, an output of each X-ray detecting element being converted into an X-ray transmission signal;

means for adjusting, element by element, irregularities of X-ray detection sensitivity of the X-ray beam detecting means in the slice thickness direction so that the X-ray detecting elements have substantially the same X-ray detection sensitivity in the slice thickness direction;

means for not only selecting at least two channel-directional lines of X-ray detecting elements from the array but also mutually combining the sensitivity-adjusted X-ray transmission signals of the selected at least two channel-directional lines of X-ray detecting elements into the X-ray transmission signals of one or more slices;

means for acquiring the selected and combined X-ray transmission signals to process the acquired X-ray transmission signals into projection data of the one or more slices; and means for producing the acquired and processed projection data into the CT image.

2. The X-ray CT scanner of claim 1, wherein each of the X-ray detecting elements has a configuration to detect the X-ray fan beam transmitted via the aperture thereof and produce an electric signal corresponding to the X-ray transmission signal.

3. The X-ray CT scanner of claim 2, wherein the adjusting means are combined with the detecting array.

4. The X-ray CT scanner of claim 3, wherein the selecting and combined means are composed of means for selecting at least three channel-directional lines of X-ray detecting elements from the array and means for mutually combining the sensitivity-adjusted X-ray transmission signals of the selected at least three channel-directional lines of X-ray detecting elements into the X-ray transmission signals of at least two slices.

5. The X-ray CT scanner of claim 4, wherein each of the X-ray detecting elements comprises a first converting element converting the transmitted X-ray beam to a light signal and a second converting element converting the light signal to an electric signal constituting the X-ray transmission signal, each of the first and second converting elements of each of all the X-ray detecting elements being disposed at a pitch corresponding to the unequal element pitch in the slice-thickness direction, and the adjusting means comprises a filter member inserted between the first and second converting elements of each X-ray detecting element, the filter member having a light-transmittance changeable depending on the unequal slice pitch.

6. The X-ray CT scanner of claim 5, wherein the light-transmittance of the filter member is controllable.

7. The X-ray CT scanner of claim 6, wherein the adjusting means comprises means for changing the light-transmittance according to at least one of a desired sensitivity distribution of the X-ray transmission signals provided to the acquiring and processing means, a scanning condition for obtaining the CT images, and a selecting condition for the X-ray transmission signals of the multi-slices selected and combined by the selecting and combining means.

8. The X-ray CT scanner of claim 7, wherein the light-transmittance changing means is constructed so as to change the light-transmittance in either every X-ray detecting element or every group of the X-ray detecting elements.

9. The X-ray CT scanner of claim 4, wherein each of the X-ray detecting elements comprises a first converting element converting the transmitted X-ray beam to a light signal and a second converting element converting the light signal to an electric signal constituting the X-ray transmission signal, each of the first and second converting elements of each of all the X-ray detecting elements being disposed at a pitch corresponding to the unequal element pitch in the slice-thickness direction, and the adjusting means is composed of means for changing a light sensitivity of each second converting element in agreement with the unequal slice pitch.

10. The X-ray CT scanner of claim 9, wherein the second converting element is a photodiode having an active area being formed of a pn junction and receiving the light signal, and the adjusting means is composed of means for changing a characteristic of the active area of each photodiode in agreement with the unequal slice pitch.

11. The X-ray CT scanner of claim 4, wherein each of the X-ray detecting elements comprises a first converting element converting the transmitted X-ray beam to a light signal and a second converting element converting the light signal to an electric signal constituting the X-ray transmission signal, the first converting element of each of all the X-ray detecting elements being disposed at an equal element pitch in the slice-thickness direction and the second converting element of each of all the X-ray detecting elements being disposed at a pitch corresponding to the unequal element pitch in the slice-thickness direction, structural differences between the disposed pitches of the first and second converting elements providing the adjusting means.

12. The X-ray CT scanner of claim 11, wherein the first converting element is a scintillator and the second converting element is a photo sensor.

13. The x-ray CT scanner of claim 9, wherein the first converting element is a scintillator having a light-emitting efficiency and the light sensitivity changing means is constructed so as to control the light-emitting efficiency in agreement with the unequal slice pitch.

14. The X-ray CT scanner or claim 9, wherein the first converting element is a scintillator on which an optical reflecting layer having a light reflecting efficiency is formed other than a light output surface thereof, and the light sensitivity changing means is constructed so as to control the light reflecting efficiency in agreement with the unequal slice pitch.

15. The X-ray CT scanner of claim 9, wherein the first converting element is a scintillator having an X-ray incidence area for receiving the X-ray transmitted beam and the light sensitivity changing means is constructed so as to control the X-ray incidence area in size in agreement with a desired sensitivity distribution for the X-ray transmission signals, provided to the acquiring means.

16. The X-ray CT scanner of claim 13, wherein the scintillators disposed in the slice-thickness direction have crosstalk-proof separators inserted between adjoining ones of the scintillators, and the light sensitivity changing means is constructed so as to control a thickness of each of the separators in the slice-thickness direction in agreement with the unequal slice pitches.

17. The X-ray CT scanner of claim 4, wherein each of the X-ray detecting elements comprises a first converting element converting the transmitted X-ray beam to a light signal and a second converting element converting the light signal to an electric signal constituting the X-ray transmission data, each of the first and second converting elements of each of all the X-ray detecting elements being disposed at a pitch corresponding to the unequal element pitch in the slice-thickness direction, and the adjusting means is composed of a member for adjusting the detection sensitivity in obtaining the electric signal constituting the X-ray transmission signal provided from each second converting element to the selecting and combining means in agreement with the unequal slice pitch, the detection sensitivity adjusting member being coupled with each second converting element.

18. The X-ray CT scanner of claim 17, wherein the detection sensitivity adjusting member is constructed so as to adjust the detection sensitivity of the electric signal in either one of every X-ray detecting element to which the signal sensitivity adjusting means is connected or every group of the X-ray detecting elements to each of which the detection sensitivity adjusting member is connected.

19. The X-ray CT scanner of claim 18, wherein the detection sensitivity adjusting member is constructed so as to adjust the detection sensitivity of the electric signal according to at least one of a desired detection sensitivity distribution of the X-ray transmission signal provided to the acquiring means, a scanning condition for obtaining the CT image, and a selecting condition for the X-ray transmission signals of the multi-slices selected and combined by the selecting and combining means.

20. The X-ray CT scanner of claim 4, wherein each of the X-ray detecting elements comprises a first converting element converting the transmitted X-ray beam to a light signal and a second converting element converting the light signal to an electric signal constituting the X-ray transmission signal, each of the first and second converting elements of each of all the X-ray detecting elements being disposed at an equal pitch in the slice-thickness direction, and the X-ray beam detecting means comprises means for mutually combining at least part or the electric signals from the second converting elements disposed in the array into the X-ray transmission signals corresponding to the multi-slices in agreement with the unequal slice pitch.

21. The X-ray CT scanner of claim 20, wherein the signal combining means of the X-ray beam detecting means has leads not only electrically combining at least two of the second converting elements disposed in the slice-thickness direction but also electrically connecting the at least two second converting elements to the selecting and combining means.

22. The X-ray CT scanner of claim 20, wherein the signal combining means of the X-ray beam detecting means consists of means for connecting output lines of the second converting elements disposed in the slice-thickness direction and output lines of the selecting and combining means with each other such that part of the second converting elements are electrically combined with each other.

23. The X-ray CT scanner of claim 2, wherein X-ray detecting elements disposed line by line along the slice-thickness direction in the array consist of a plurality of specified X-ray detecting elements of which aperture widths are the same in the slice thickness direction.

24. The X-ray CT scanner of claim 23, wherein each of the X-ray detecting elements comprises a first converting element converting the transmitted X-ray beam to a light signal and a second converting element converting the light signal to an electric signal constituting the X-ray transmission signal.

25. The X-ray CT scanner of claim 24, wherein the first converting element is a scintillator and the second converting element is a photo sensor.

26. The X-ray CT scanner of claim 25, wherein the adjusting means comprises a combining lead member for not only electrically combining line by line outputs of the photo sensors corresponding to the specified X-ray detecting elements according to the unequal slice pitch but also providing the combined outputs to the selecting and combining means.

27. The X-ray CT scanner of claim 9, wherein the first converting element is a scintillator having a light transmittance, and the light sensitivity changing means is constructed so an to control the light transmittance in agreement with the unequal slice pitch.

28. The X-ray CT scanner of claim 26, wherein each of the photo sensors has a light incidence area and each of the light incidence areas of the photo sensors positionally corresponding to the specified X-ray detecting elements is in part covered by a light-reflecting member to reflect the light signal.

29. The X-ray CT scanner of claim 28, wherein the light-reflecting member is placed to cover both slice-thickness directional edges of the light incidence area of each of the photo sensors.

30. The X-ray CT scanner of claim 23, wherein X-ray detecting elements disposed in the slice-thickness direction in the array are classified into two types in the aperture width, one type of which being formed by the specified X-ray detecting elements.

31. The X-ray CT scanner of claim 30, wherein the one type of the X-ray detecting elements have double the aperture width of each of the other type of the X-ray detecting elements in each line.

32. The X-ray CT scanner of claim 2, wherein X-ray detecting elements disposed in the slice-thickness direction in the array consist of a plurality of types of X-ray detecting elements in the aperture width, X-ray detecting elements of the narrowest aperture width being disposed in a central portion in the slice direction of the array.

33. The X-ray CT scanner of claim 32, wherein X-ray detecting elements having aperture widths larger than the narrowest aperture width are disposed in both outer ranges of the central portion, in turn, depending on largeness of the aperture widths, toward each outer side in the slice thickness direction.

34. The X-ray CT scanner of claim 33, wherein the X-ray detecting elements disposed in the central portion are 1 mm as the narrowest aperture width and eight in number, and the X-ray detecting elements having aperture widths larger than the narrowest aperture width are composed of a plurality of width types of X-ray detecting elements of which aperture widths increase at a multiple $2^k$ (k=1, 2, 3) mm, each width type of X-ray detecting elements being four in number.

35. The X-ray CT scanner of claim 34, wherein all the x-ray detecting elements disposed along each line in the slice thickness direction are made up of, viewing from one side in the slice thickness direction, two 8 mm-width elements, two 4 mm-width elements, two 2 mm-width elements, eight 1 mm-width elements, two 2 mm-width elements, two 4 mm-width elements, and two 8 mm-width elements.

36. The X-ray CT scanner of claim 1, wherein the acquiring means comprises a data acquisition system having a plurality of data acquiring elements two-dimensionally disposed in both the slice-thickness and channel directions, the data acquiring elements receiving the selected and combined X-ray transmission signals.

37. An X-ray CT scanner for obtaining a computed tomography (CT) image of a subject, the scanner comprising:

an X-ray source radiating an X-ray fan beam spreading in a slice-thickness direction;

a scanning system to scan the subject with the X-ray fan beam;

a detector to detect the X-ray fan beam transmitted through the subject with a detecting element array including a plurality of X-ray detecting elements two-dimensionally disposed in the slice-thickness direction and a channel direction orthogonal to the slice thickness direction, the X-ray detecting elements of the array being classified in the slice-thickness direction into a plurality of groups each including at least one channel-directional line of X-ray detecting elements each of which has an aperture to receive the X-ray fan beam, the aperture being changed in width in the slice-thickness direction on a basis of an unequal element pitch when viewed group by group, an output of each X-ray detecting element being converted into an X-ray transmission signal;

an adjusting member to adjust, element by element, irregularities of X-ray detection sensitivity of the detector in the slice thickness direction so that the X-ray detecting elements have substantially the same X-ray detection sensitivity in the slice thickness direction;

a switch unit to not only select at least two channel-directional lines of X-ray detecting elements from the array but also mutually combine the sensitivity-adjusted X-ray transmission signals of the selected at least two channel-directional lines of X-ray transmission signals of one or more slices;

a data acquisition system to acquire the selected and combined X-ray transmission signals selected and combined by the switch unit to process the acquired X-ray transmission signals into projection data of the one or more slices; and a producing unit producing the acquired and processed projection data into the CT image.

* * * * *